(12) United States Patent
Reiche

(10) Patent No.: US 11,759,474 B2
(45) Date of Patent: Sep. 19, 2023

(54) USE OF SGLT-2 INHIBITORS IN THE DRYING-OFF OF NON-HUMAN MAMMALS

(71) Applicant: Boehringer Ingelheim Vetmedica GmbH, Ingelheim am Rhein (DE)

(72) Inventor: Dania Birte Reiche, Bingen am Rhein (DE)

(*) Notice: Subject to any disclaimer, the term of this patent is extended or adjusted under 35 U.S.C. 154(b) by 173 days.

(21) Appl. No.: 17/104,414

(22) Filed: Nov. 25, 2020

(65) Prior Publication Data

US 2021/0161930 A1 Jun. 3, 2021

(30) Foreign Application Priority Data

Oct. 5, 2020 (EP) .................................... 20200103

(51) Int. Cl.
| | |
|---|---|
| *A61K 31/7048* | (2006.01) |
| *A23K 20/24* | (2016.01) |
| *A23K 20/121* | (2016.01) |
| *A61P 15/14* | (2006.01) |
| *A61K 31/351* | (2006.01) |
| *A61K 31/381* | (2006.01) |
| *A61K 31/7056* | (2006.01) |

(Continued)

(52) U.S. Cl.
CPC ........ *A61K 31/7048* (2013.01); *A23K 20/121* (2016.05); *A23K 20/24* (2016.05); *A61K 31/351* (2013.01); *A61K 31/381* (2013.01); *A61K 31/382* (2013.01); *A61K 31/7028* (2013.01); *A61K 31/7034* (2013.01); *A61K 31/7042* (2013.01); *A61K 31/7056* (2013.01); *A61P 15/14* (2018.01)

(58) Field of Classification Search
CPC ....... A61P 15/14; A61K 3/10; A61K 31/7048; A61K 31/351; A61K 31/381; A61K 31/382; A61K 31/7028; A61K 31/7034; A61K 31/7024; A61K 31/7056
See application file for complete search history.

(56) References Cited

U.S. PATENT DOCUMENTS

| | | | |
|---|---|---|---|
| 6,391,849 B1 | 5/2002 | Shamay et al. | |
| 8,133,916 B1 | 3/2012 | Horseman et al. | |

(Continued)

FOREIGN PATENT DOCUMENTS

| | | |
|---|---|---|
| EP | 2349272 | 3/2011 |
| EP | 2675527 | 12/2013 |

(Continued)

OTHER PUBLICATIONS

Bradford et al., "Phlorizin Administration Increases Hepatic Gluconeogenic Enzyme mRNA Abundance but Not Feed Intake in Late-Lactation Dairy Cows" Journal of Nutrition vol. 135 pp. 2206-2211 (Year: 2005).*

(Continued)

*Primary Examiner* — Eric Olson
(74) *Attorney, Agent, or Firm* — Katrina Bergbauer

(57) ABSTRACT

The present invention is directed to the use of at least one SGLT-2 inhibitor in a non-human mammal, preferably ruminant, preferably for drying-off of a non-human mammal, preferably ruminant, as well as corresponding methods, such as improving and/or facilitating the drying-off of a non-human mammal, preferably ruminant, comprising administering to such non-human mammal, preferably ruminant, at least one SGLT-2 inhibitor.

25 Claims, 2 Drawing Sheets

(51) Int. Cl.
*A61K 31/382* (2006.01)
*A61K 31/7028* (2006.01)
*A61K 31/7034* (2006.01)
*A61K 31/7042* (2006.01)

(56) References Cited

U.S. PATENT DOCUMENTS

| | | |
|---|---|---|
| 9,487,557 B2 | 11/2016 | Iscovich et al. |
| 9,744,158 B2 | 8/2017 | Lagarde et al. |
| 2004/0258778 A1 | 12/2004 | Farmar et al. |
| 2011/0245261 A1 | 10/2011 | Lagarde et al. |
| 2014/0024670 A1 | 1/2014 | Isaka et al. |

FOREIGN PATENT DOCUMENTS

| | | |
|---|---|---|
| WO | 2004113378 | 12/2004 |
| WO | 2007128749 | 11/2007 |
| WO | 2009143020 A1 | 11/2009 |
| WO | 2014016381 | 1/2014 |
| WO | 2015173584 A1 | 11/2015 |
| WO | 2016104643 A1 | 6/2016 |
| WO | 2017156632 | 9/2017 |
| WO | 2019121509 | 6/2019 |

OTHER PUBLICATIONS

Melissa Elischer, "The Holstein Dairy Cow" downloaded from sites.udel.edu/canr-animalscience/2016/04/07/the-holstein-dairy-cow/ (Year: 2016).*
Nommsen-Rivers et al., "Feasibility and Acceptability of Metformin to Augment Low Milk Supply: A Pilot Randomized Controlled Trial" Journal of Human Lactation vol. 35 No. 2 pp. 261-271 DOI: 10.1177/0890334418819465 (Year: 2019).*
Lau et al., "Effects of Diabetes Mellitus on Lactation in the Rat" Diabetes and Lactation vol. 204 pp. 81-89 (Year: 1993).*
Zhao F. -Q. et al.: "Cloning and Expression of Bovine Sodium/Glucose Cotransporter SGLT2", Journal of Dairy Science; vol. 88, No. 8, Aug. 1, 2005, p. 2738-2748.
Gross J. J. et al.: "Glucose transport and milk secretion during manipulated plasma insulin and glucose concentrations and during LPS induced mastitis in dairy cows", Journal of Animal Physiology and Animal Nutrition; vol. 99, No. 4, Aug. 1, 2015; p. 747-756.
Bertulat S. et al.: "Effect of a single injection of cabergoline at dry off on udder characteristics in high-yielding dairy sows", J Dairy Sci 2017, 100(4): 3220-3232.
Lanctôt S. et al.: "Effect of intramammary infusion of chitosan hydrogels at drying-off on bovine mammary gland nvolution", J Dairy Sci 2017, 100(3): 2269-2281.
Maynou G. et al.: "Effects of oral adminislialion of acidogenic boluses at dry-off on performance and behavior of dairy cattle", J Dairy Sci 2018, 101(12): 1-12.
Zhao F. -Q.: "Biology of Glucose Transport in the Mammary Gland", J Mammary Gland Biol Neoplasia 2014, 19: 3-17.
Azzalin A. et al., "Inhibitors of GLUT/SLC2A Enhance the Action of BCNU and Temozolomide against High-Grade Gliomas," Neoplasia, vol. 19, No. 4, 2017, pp. 364-373.

* cited by examiner

USE OF SGLT-2 INHIBITORS IN THE DRYING-OFF OF NON-HUMAN MAMMALS

FIELD OF THE INVENTION

The invention relates to the field of medicine, in particular to the field of veterinary medicine. The invention relates to the use of one or more SGLT-2 inhibitors or a pharmaceutically acceptable form thereof in the drying-off of a non-human mammal, preferably ruminants, more preferably a ruminant.

BACKGROUND INFORMATION

In dairy cows, the duration of lactation is usually approximately 10 months. After this period of lactation, milking of the animal is often stopped abruptly, the backpressure of milk accumulating in the udder being an important stimulate for involution of mammary cells to stop producing milk. The start of the dry period is a challenge for the health of ruminants. Udder engorgement and pain after drying off and/or milk leakage potentially leading to intra-mammary microbial infections and mastitis is a thread especially in dairy cattle with high milk yield. For every 5 kg of milk yield over 12.5 kg at dry-off, the odds of an intra-mammary infection is increased by at least 77%.

As in other species, the sodium glucose linked transporter number 2 (SGLT-2) is predominantly expressed in the bovine kidney. However, it is expressed at lower levels in the bovine mammary gland, liver, lung, spleen, intestine, and skeletal muscle. The expression of SGLT-2 in the bovine mammary gland is increased more than 10-fold from late pregnancy to early lactation (Zhao F Q et al., J. Dairy Sci., 2005, 88: 2738-2748). However, the physiological roles of the SGLTs in the mammary gland remain to be studied (Zhao F Q, J Mammary Gland Biol Neoplasia 2014, 19: 3-7).

The current state of the art is "good management"—i.e. progressive/gradual cessation of milking, and/or feed reduction. These procedures need several days to yield effects and, therefore, most often these management tools are not implemented because of convenience, but dairy cow are subject to a sudden, abrupt dry-off.

Besides, these good management procedures have clear drawbacks. The gradual cessation of milking does increase the somatic cell count, i.e. there is eventual commercial penalties to the milk price achieved. Intermitted udder engorgement also clearly induces discomfort and stress. There are controversies about the effects on milk leakage and/or incidence of intra-mammary infections. Similarly, feed restriction induces stress and discomfort. Moreover, controversial reports are available of effects on milk leakage and, consequently, the risk for intra-mammary infections. More important, feed restriction as needed for several days to effectively reduce the milk production clearly induces a negative energy balance. If this persists over several days, the increase in blood non-esterified fatty acids (NEFAs) and ketone bodies may even induce "fatty liver syndrome" and/or impair the general immune status. In addition, to what is described above also abrupt dry-off and painful udder engorgement also induces stress and stress is known to increase the susceptibility of animals to infections and, thus, adds on to the risk intra-mammary infections at start of the dry period. Thus, cows at dry-off are prone for mastitis/metritis. For instance, also subclinical mastitis or subclinical ketosis are often unrecognized but may have negative effects even on long term—i.e. the subsequent reproduction cycle/fertility and milk yield and/or milk quality.

Drugs with prolactin inhibitory effects like cabergoline may be used. Cabergoline is a synthetic ergot derivative, which is a potent dopamine receptor agonist on D2 receptors. It acts on dopamine receptors of prolactin producing cells in the pituitary gland suppressing the prolactin production. Consequently, cabergoline administration induces a reduction of milk production leading to a reduction in udder engorgement and intra-mammary pressure at dry-off. Cabergoline is registered in some countries for use in dairy cows as an aid in the abrupt drying-off by reducing milk production to reduce milk leakage at drying off, reduce the risk of new intra-mammary infections (IMI) during the dry period and reduce discomfort. However, the marketing authorizations for cabergoline in the EU were suspended in 2016 due to serious adverse effects, including the death of several cows.

Further prior art is as follows:
Bertulat S et al., (J Dairy Sci 2017, 100(4): 3220-3232) describe the effect of a single injection of cabergoline at dry-off on udder characteristics in high-yielding dairy cows.
EP 2 349 272 B1 relates to a veterinary composition comprising cabergoline for a use to induce lactation depletion and promoting mammary involution in gestating ruminants.
EP 2 675 527 B1 relates to the use of a veterinary composition comprising cabergoline to be administered to a ruminant in a specific dosage regimen.
Gross J J et al. (J Anim Physiol Anim Nutr 2015, 99: 747-756) disclose the glucose transport and milk secretion during manipulated plasma insulin and glucose concentrations and during LPS-induced mastitis in dairy cows.
Lanctôt S et al. (J Dairy Sci 2017, 100(3): 2269-2281) describes the effect of intra-mammary infusion of chitosan hydrogels at drying-off on bovine mammary gland involution.
Maynou G et al. (J Dairy Sci 2018, 101(12): 1-12) describe the effects of oral administration of acidogenic boluses at dry-off on performance and behavior of dairy cattle.
US 2004/0258778 A1 relates to lactation cessation and breast engorgement compositions based on cabbage extract and methods of use thereof.
US 2011/0245261 A1 relates to an antiprolactinic veterinary composition to be administered to ruminants.
US 2014/0024670 A1 relates to a veterinary anti-prolactin composition to be administered to ruminants.
U.S. Pat. No. 4,412,993 A describes methods of treating pseudopregnancy, galactorrhea and mastitis in mammals, in particular the dog.
U.S. Pat. No. 6,391,849 B1 relates to a method and pharmaceutical composition for disrupting lactation in a mammary gland and for treating and preventing mastitis.
U.S. Pat. No. 8,133,916 B1 relates to the control of milk production and mammary involution.
U.S. Pat. No. 9,487,557 B2 describes novel short peptides that are highly effective in inducing involution in a mammary gland of a lactating mammal and cessation of milk production by the gland.
U.S. Pat. No. 9,744,158 B2 describes an antiprolactinic veterinary composition to be administered to ruminants.
WO 2004/113378 A2 relates to three novel peptides identified from cow's milk for use in the modulation of the milk secretion rate of a lactating cell.

WO 2009/143020 A1 discloses methods for treating hyperuricemia employing an SGLT-2 inhibitor alone or in combination with a supply of carbohydrate and/or in combination with an inhibitor of uric acid synthesis.

WO 2015/173584 A1 discloses methods for avoiding an increase in glucagon associated with the administration of an SGLT-2 inhibitor via the co-administration of a DPP-IV inhibitor.

WO 2016/104643 A1 discloses solid preparations for treating diabetes.

WO 2017/156632 A1 describes a method of preventing intra-mammary infection and accelerating involution by administration of a biological response modifier, specifically a chitosan solution to the teat of a lactating mammal at drying-off.

Thus, there is a medical need for a safe, convenient and effective aid to reduce the risks for animal/udder/mammary gland health and increase animal welfare with a management of sudden dry-off in non-human mammals, preferably ruminants, which overcomes the problems of the prior art.

SUMMARY OF THE INVENTION

The present invention concerns the use of at least one SGLT-2 inhibitor in a non-human mammal, preferably ruminants, more preferably a ruminant, even more preferably for drying-off of a non-human mammal, even more preferably ruminants, most preferably a ruminant.

A corresponding method of drying-off of a non-human mammal, preferably ruminants, more preferably a ruminant, comprising administering at least one SGLT-2 inhibitor, a corresponding at least one SGLT-2 inhibitor for use in a method of drying-off of a non-human mammal, preferably ruminants, more preferably a ruminant, as well as the corresponding use of at least one SGLT-2 inhibitor for the preparation of a medicament for drying-off of a non-human mammal, preferably ruminants, more preferably a ruminant, are also intended to be comprised by the present invention.

The present invention also concerns a method of improving and/or facilitating the drying-off of a non-human mammal, preferably ruminants, more preferably a ruminant, comprising administering to such a non-human mammal, preferably ruminant(s) at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of improving and/or facilitating the drying-off of a non-human mammal, preferably ruminants, more preferably a ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for improving and/or facilitating the drying-off of a non-human mammal, preferably ruminants, more preferably a ruminant, wherein such at least one SGLT-2 inhibitor is administered to a non-human mammal, preferably ruminants, more preferably a ruminant, are also intended to be comprised by the present invention.

The present invention also concerns a method of reducing the milk production, preferably milk production and/or secretion, in a pregnant and/or a lactating non-human mammal, preferably ruminants, more preferably a pregnant and/or lactating ruminant, comprising administering to such non-human mammal, preferably ruminant(s), at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of reducing the milk production, preferably milk production and/or secretion, in a pregnant and/or a lactating non-human mammals, preferably ruminants, more preferably a pregnant and/or lactating ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for reducing the milk production, preferably milk production and/or secretion, in a pregnant and/or a lactating non-human mammal, preferably ruminants, more preferably a pregnant and/or lactating ruminant, wherein such at least one SGLT-2 inhibitor is administered to a non-human mammal, preferably ruminants, more preferably a ruminant, are also intended to be comprised by the present invention.

The present invention also concerns a method of decreasing milk accumulation and/or engorgement in the udder, preferably udder and/or mammary gland, of a non-human mammal, preferably ruminants, more preferably a ruminant, comprising administering to such non-human mammal, preferably ruminant(s) at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of decreasing milk accumulation and/or engorgement in the udder, preferably udder and/or mammary gland, of a non-human mammal, preferably ruminants, more preferably a ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for decreasing milk accumulation and/or engorgement in the udder, preferably udder and/or mammary gland, of a non-human mammal, preferably ruminants, more preferably a ruminant, wherein such at least one SGLT-2 inhibitor is administered to a non-human mammal, preferably ruminants, more preferably a ruminant, are also intended to be comprised by the present invention.

The present invention also concerns a method of decreasing the discomfort associated with udder engorgement, such as increasing the daily lying time and/or reduction of stress, of a non-human mammal, preferably ruminants, more preferably a ruminant, comprising administering to such non-human mammal, preferably ruminant(s) at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of decreasing the discomfort associated with udder engorgement, such as increasing the daily lying time and/or reduction of stress, of a non-human mammal, preferably ruminants, more preferably a ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for decreasing the discomfort associated with udder engorgement, such as increasing the daily lying time and/or reduction of stress, of a non-human mammal, preferably ruminants, more preferably a ruminant, wherein such at least one SGLT-2 inhibitor is administered to a non-human mammal, preferably ruminants, more preferably a ruminant, are also intended to be comprised by the present invention.

The present invention also concerns a method of decreasing milk leakage after drying-off of a non-human mammal, preferably ruminants, more preferably a ruminant, comprising administering to such non-human mammal, preferably ruminant(s) at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of decreasing milk leakage after drying-off of a non-human mammal, preferably ruminants, more preferably a ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for decreasing milk leakage after drying-off of a non-human mammal, preferably ruminants, more preferably a ruminant, wherein such at least one SGLT-2 inhibitor is administered to a non-human mammal, preferably ruminants, more preferably a ruminant, are also intended to be comprised by the present invention.

The present invention also concerns a method of decreasing the incidence of intra-mammary infections (IMI), preferably mastitis and/or metritis, in a non-human mammal, preferably ruminants, more preferably a ruminant, comprising administering to such non-human mammal, preferably ruminant(s) at least one SGLT-2 inhibitor.

A corresponding use of at least one SGLT-2 inhibitor, wherein such at least one SGLT-2 inhibitor is administered to a non-human mammal, preferably ruminants, more preferably a ruminant, a corresponding at least one SGLT-2 inhibitor for use in a method of decreasing the incidence of intra-mammary infections (IMI), preferably mastitis and/or metritis, in a non-human mammal, preferably ruminants, more preferably a ruminant, wherein such at least one SGLT-2 inhibitor is administered to a non-human mammal, preferably ruminants, more preferably a ruminant, as well as the corresponding use of at least one SGLT-2 inhibitor for the preparation of a medicament for decreasing the incidence of intra-mammary infections (IMI), preferably mastitis and/or metritis, in a non-human mammal, preferably ruminants, more preferably a ruminant, wherein such at least one SGLT-2 inhibitor is administered to a non-human mammal, preferably ruminants, more preferably a ruminant, are also intended to be comprised by the present invention.

In one aspect, the present invention also concerns the use or methods as herein disclosed and/or claimed, wherein the at least one SGLT-2 inhibitor is administered in a therapeutically effective amount without exerting any harmful and/or abortifacient effects on a pregnant non-human mammal, preferably ruminant(s), and/or wherein the at least one SGLT-2 inhibitor is administered in a therapeutically effective amount without exerting any negative effects on the subsequent reproduction cycle/fertility and milk yield and/or milk quality in the next lactation.

In one aspect, the present invention also concerns the use or methods as herein disclosed and/or claimed, wherein the at least one SGLT-2 inhibitor is administered in a therapeutically effective amount that additionally or alternatively effects a reduction of the incidence of new intra-mammary infections (IMI) or mastitis in the first month after start of the next lactation.

In one aspect, the present invention also concerns the use or methods as herein disclosed and/or claimed, wherein the at least one SGLT-2 inhibitor is selected from the group consisting of:

(1) a glucopyranosyl-substituted benzene derivative of the formula (1)

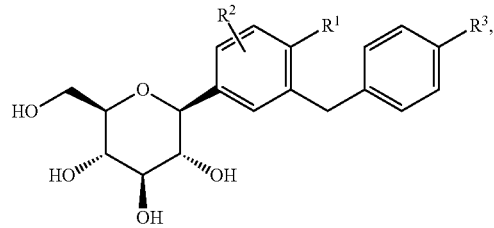

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

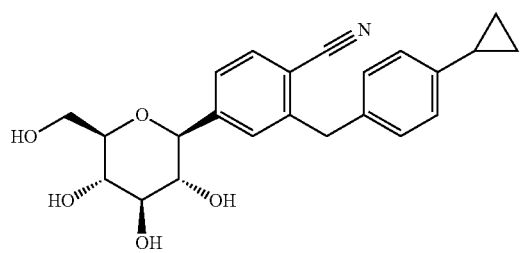 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):
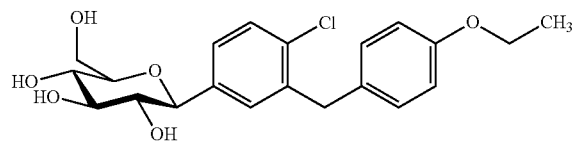
(4) Canagliflozin, represented by formula (4):
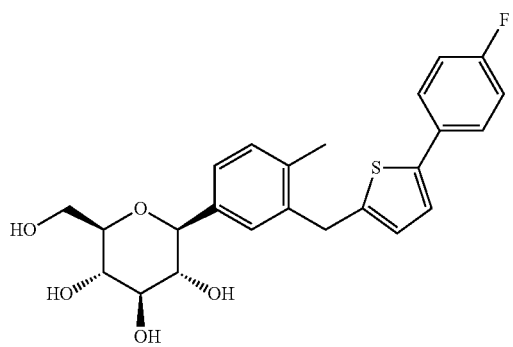 [SMILES: Cc1ccc([C@@H]2O[C@H](CO)[C@@H](O)[C@H](O)[C@H]2O)cc1Cc1ccc(-c2ccc(F)cc2)s1]
(5) Empagliflozin, represented by formula (5):
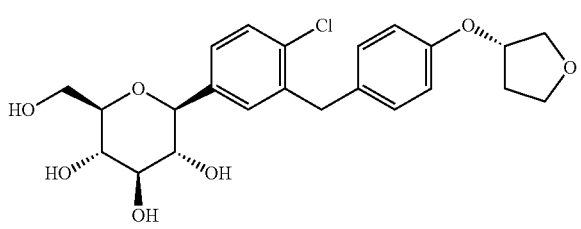 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
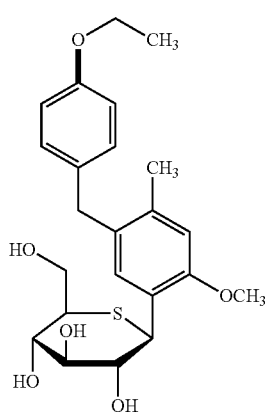
(7) Tofogliflozin, represented by formula (7):
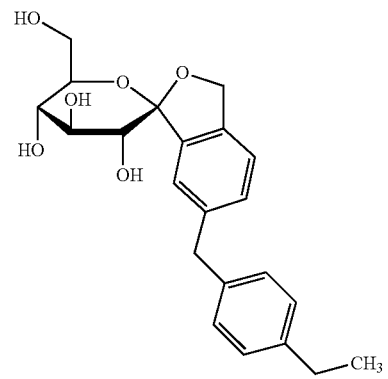
(8) Ipragliflozin, represented by formula (8):
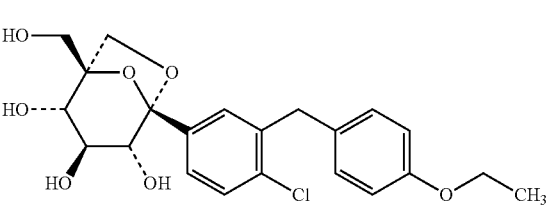 [SMILES: CCOc1ccc(Cc2cc([C@]34OC[C@](CO)(O3)[C@@H](O)[C@H](O)[C@H]4O)ccc2Cl)cc1]
(9) Ertugliflozin, represented by formula (9):
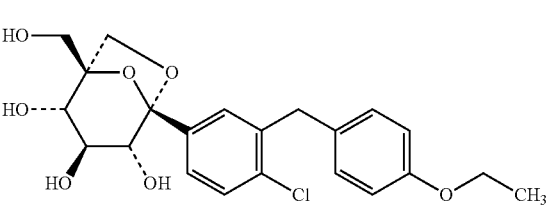 [SMILES: CCOc1ccc(Cc2cc([C@]34OC[C@](CO)(O3)[C@@H](O)[C@H](O)[C@H]4O)ccc2Cl)cc1]
(10) Atigliflozin, represented by formula (10):
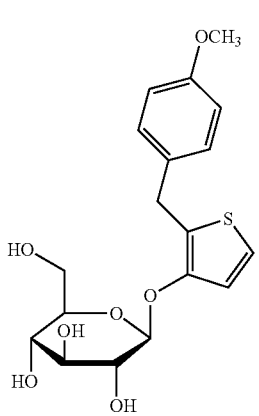

(11) Remogliflozin, represented by formula (11):

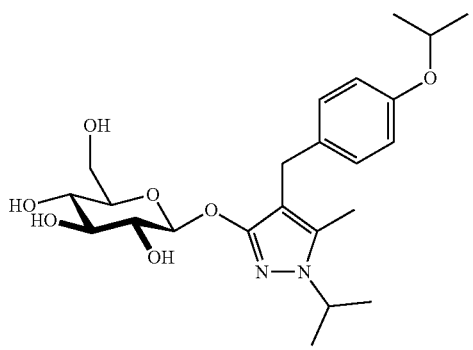

(11A) Remogliflozin etabonate, represented by formula (11A):

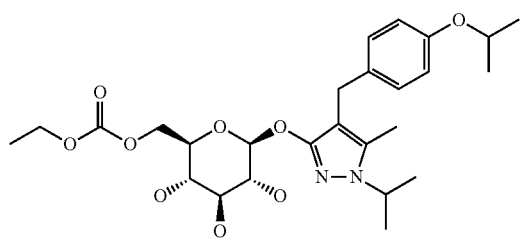 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

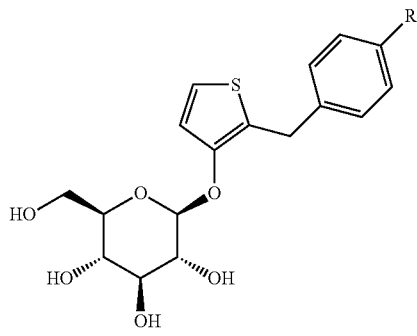

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

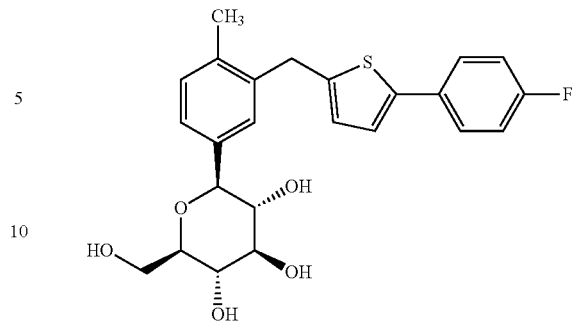

(14) a spiroketal derivative of the formula (14):

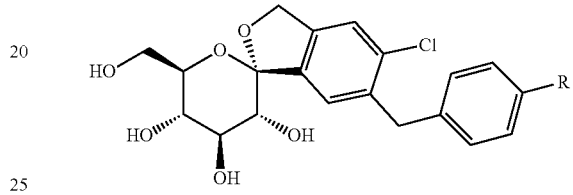

wherein R denotes methoxy, trifluoromethoxy, ethoxy, ethyl, isopropyl or tert. butyl;

(15) a pyrazole-O-glucoside derivative of the formula (15)

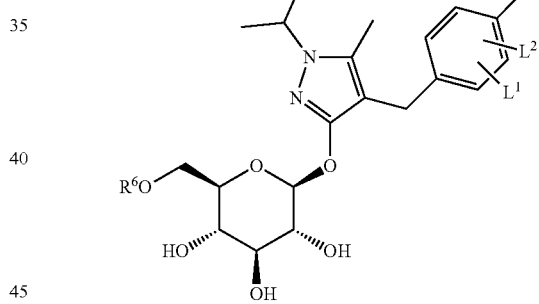

wherein
R$^1$ denotes C$_1$-alkoxy,
L$^1$, L$^2$ independently of each other denote H or F,
R$^6$ denotes H, (C$_{1-3}$-alkyl)carbonyl, (C$_{1-6}$-alkyl)oxycarbonyl, phenyloxycarbonyl, benzyloxycarbonyl or benzylcarbonyl;

(16) Sotagliflozin, represented by formula (16):

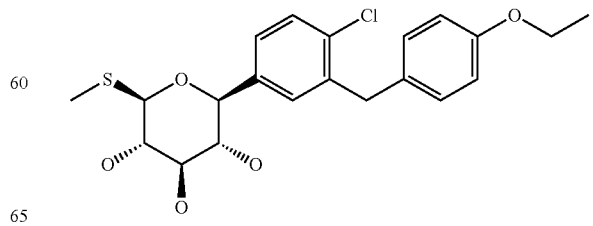

(17) Sergliflozin, represented by formula (17):

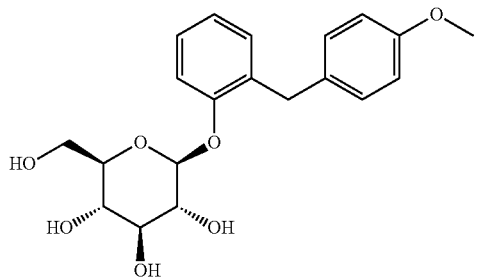 [SMILES: COc1ccc(Cc2ccccc2O[C@@H]2O[C@H](CO)[C@@H](O)[C@H](O)[C@H]2O)cc1]

(18) a compound represented by formula (18):

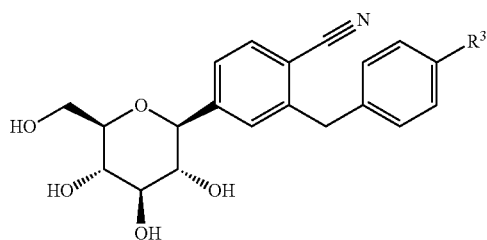

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxyethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, wherein R³ is preferably selected from cyclopropyl, ethyl, ethinyl, ethoxy, (R)-tetrahydrofuran-3-yloxy or (S)-tetrahydrofuran-3-yloxy; and R³ most preferably is cyclopropyl,
or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(19) Bexagliflozin, represented by formula (19):

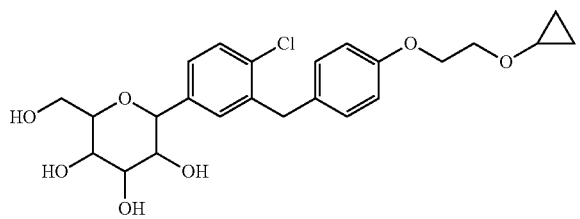 [SMILES: OCC1OC(c2ccc(Cl)c(Cc3ccc(OCCOC4CC4)cc3)c2)C(O)C(O)C1O]

(20) Janagliflozin, represented by formula (20):

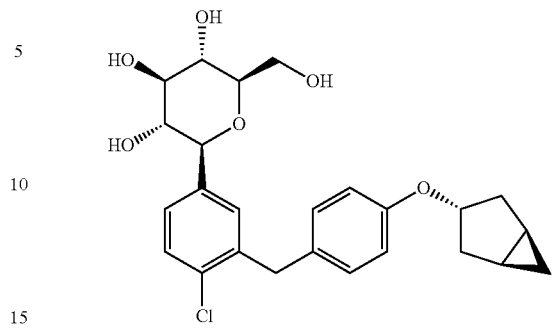

(21) Rongliflozin,
(22) Wanpagliflozin.

In one aspect, the present invention also concerns the use or methods as herein disclosed and/or claimed, wherein the non-human mammal, preferably ruminant(s), is/are selected from the group consisting of: bovine, canine, caprine, equine, feline, lagomorphs, ovine, porcine, rodent; preferably selected from the group consisting of: cattle, cow, dog, goat, horse, pony, donkey, cat, sheep, pig, rabbit, rat, mouse; more preferably selected from the group consisting of bovine, caprine, ovine, even more preferably selected from the group consisting of: cattle, cow(s), goat(s), sheep; even more preferably selected from the group consisting of: dairy cattle, pregnant and/or lactating dairy cattle; most preferably selected from the group consisting of: cow(s), pregnant and/or lactating cow(s).

In one aspect, the present invention also concerns the use or methods as herein disclosed and/or claimed, wherein the at least one SGLT-2 inhibitor is administered orally, parenterally, rectally, intravaginally, intravenously, subcutaneously or intramuscularly, preferably subcutaneously, intramuscularly or intravenously.

In one aspect, the present invention also concerns the use or methods as herein disclosed and/or claimed, wherein the at least one SGLT-2 inhibitor is administered at a dose of 0.01 mg/kg bodyweight to 10 mg/kg bodyweight, preferably at a dose of 0.01 mg/kg bodyweight to 5 mg/kg bodyweight, more preferably at a dose of 0.01 mg/kg bodyweight to 3 mg/kg bodyweight, even more preferably at a dose of 0.03 mg/kg bodyweight to 3 mg/kg bodyweight, most preferably at a dose of 0.03 mg/kg bodyweight or 0.3 mg/kg bodyweight or 3 mg/kg bodyweight.

In one aspect, the present invention also concerns the use or methods as herein disclosed and/or claimed, wherein the at least one SGLT-2 inhibitor is administered once, twice, three-times, four-times, five-times, six-times or daily for a week, preferably once only at start of drying-off or twice as two treatments 24 hours or 48 hours apart after last milking.

In one aspect, the present invention also concerns the use or methods as herein disclosed and/or claimed, wherein the at least one SGLT-2 inhibitor is velagliflozin and velagliflozin is administered as single SGLT-2 inhibitor, preferably orally, subcutaneously or intramuscularly, once only at start of drying-off or twice (24 h or 48 h apart) at a dose of 0.01 mg/kg bodyweight to 5 mg/kg bodyweight, more preferably 0.03 mg/kg bodyweight to 3 mg/kg bodyweight, even more preferably at a dose of 0.03 mg/kg bodyweight or 0.3 mg/kg bodyweight or 3 mg/kg bodyweight.

In one aspect, the present invention also concerns the use or methods as herein disclosed and/or claimed, wherein the at least one SGLT-2 inhibitor is administered before, after or concomitantly with administering at least one feed supplement, such as Bovikalc® Dry, to the non-human mammal, preferably ruminant(s), and/or before, after or concomitantly with a reduction in feed offered to the non-human mammal, preferably ruminant(s).

In one aspect, the present invention also concerns the use or methods as herein disclosed and/or claimed, wherein the feed supplement comprises one or more acidifying agents selected from the group consisting of: ammonium chloride, calcium chloride and/or calcium sulfate, more preferably comprises ammonium chloride and calcium chloride and calcium sulfate, even more preferably comprises 5% (w/w) to 15% (w/w) ammonium chloride and 40% (w/w) to 60% (w/w) calcium chloride and 15% (w/w) to 25% (w/w) calcium sulfate, most preferably comprises 10.4% (w/w) ammonium chloride and 51.9% (w/w) calcium chloride and 20.1% (w/w) calcium sulfate.

The advantages according to the present invention are one or more of the following:
- facilitates the start of the dry period at the end of lactation in a non-human mammal, preferably ruminant, with a safe, effective and convenient parenteral injection of at least one SGLT2 inhibitor;
- overcomes the problems that even good management procedures have drawbacks, such as an increase of the somatic cell counts while still delivering milk in gradual cessation of milking prior to dry-off;
- ameliorates discomfort and stress related good management as well as abrupt dry-off, which is known to impact the immune status negatively;
- increases the daily lying time and reduces stress, preferably on the days after dry-off,
- improves the immune status and/or liver function of a non-human mammal, preferably ruminant, more preferably dairy cow(s), after dry-off;
- avoids scenarios like feed reduction induced negative energy balance with eventually excessive increase in blood non-esterified fatty acids (NEFAs) and ketone bodies that may even induce "fatty liver syndrome" and/or impair the general immune status;
- advantageously influences the long-time performance of a non-human mammal, preferably ruminant, by avoiding the negative impact on subsequent reproduction cycle/fertility and milk yield and/or milk quality in the next lactation.

DETAILED DESCRIPTION OF THE INVENTION

Before the embodiments of the present invention are described in further detail, it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In the course of the present invention, "drying-off" is defined as follows: cessation of milking, preferably milk secretion, of a lactating non-human mammal, preferably ruminant.

In the course of the present invention "improving and/or facilitating the drying-off" is defined as follows: faster reduction of milk production, preferably milk secretion.

In the course of the present invention the term "mastitis" refers to the inflammation of the mammary gland caused by intra-mammary infection (IMI) with pathogens, mostly bacteria, but also yeast, fungi, or even algae. "Mastitis" is herein used to describe all forms of such inflammation, including subclinical and clinical mastitis, clinical mastitis including mild, severe and chronic mastitis.

In the course of the present invention the term "udder engorgement" or "engorgement in the udder" refers to the excessive accumulation of milk in the mammary gland, leading to pain and discomfort and/or milk leakage from the teats; also interchangeably, the term increased udder pressure is used.

In the course of the present invention the term "treatment effects" refers to an improvement and/or reduction of a condition or incidence, and/or the improvement, reduction or increase of any effect, index, marker level or other parameter relating to a condition. SGLT-2 inhibitors for use according to the invention include, but are not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940, WO 2009/022020 or WO 2009/022008.

Moreover, the one or more SGLT-2 inhibitors for use according to the invention may be selected from the group consisting of the following compounds or pharmaceutically acceptable forms thereof:
(1) a glucopyranosyl-substituted benzene derivative of the formula (1)

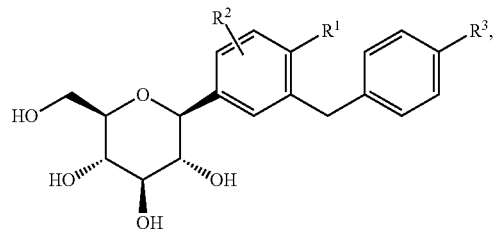

wherein $R^1$ denotes cyano, Cl or methyl (most preferably cyano);
$R^2$ denotes H, methyl, methoxy or hydroxy (most preferably H) and
$R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

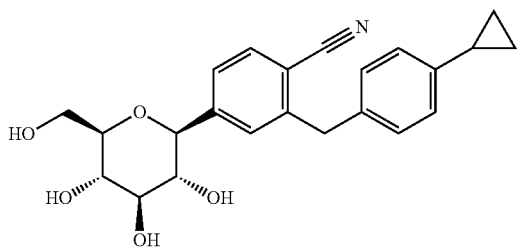 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

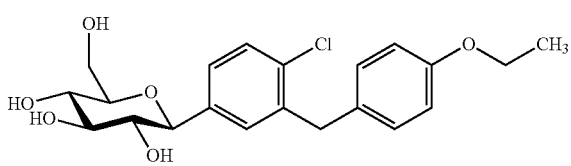

(4) Canagliflozin, represented by formula (4):

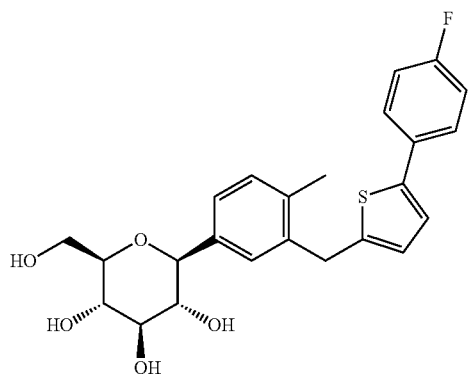 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

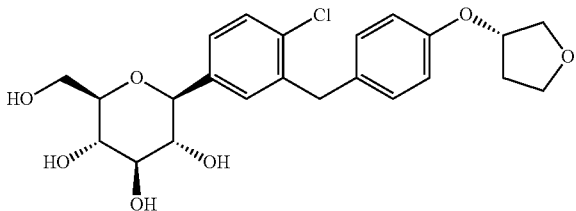 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

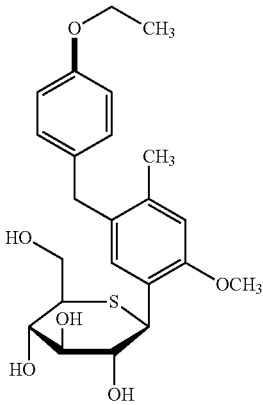

(7) Tofogliflozin, represented by formula (7):

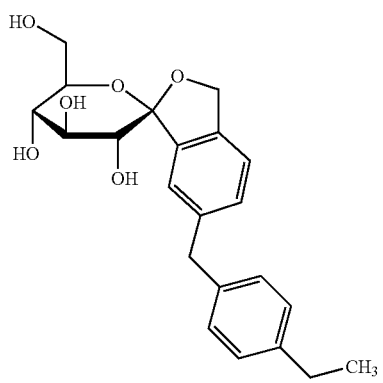

(8) Ipragliflozin, represented by formula (8):

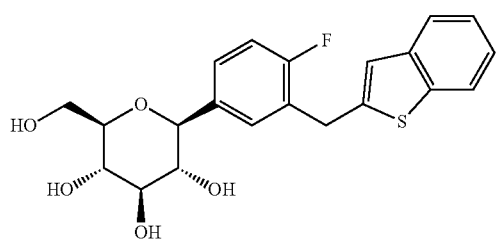 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

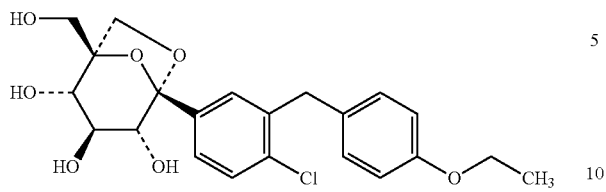

(10) Atigliflozin, represented by formula (10):

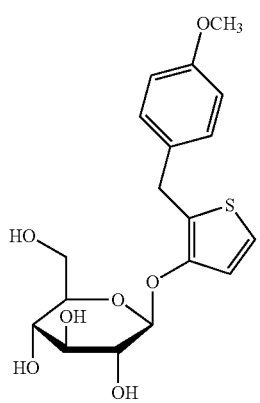

(11) Remogliflozin, represented by formula (11):

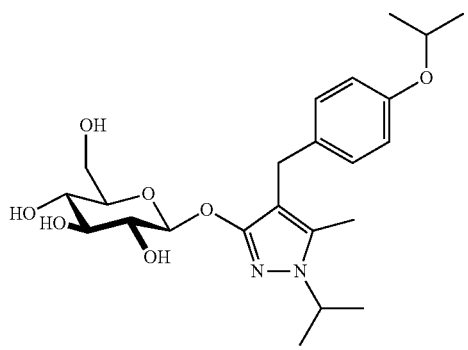

(11A) Remogliflozin etabonate, represented by formula (11A):

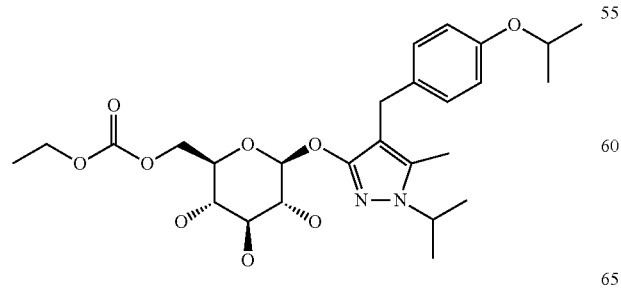

(12) a thiophene derivative of the formula (12)

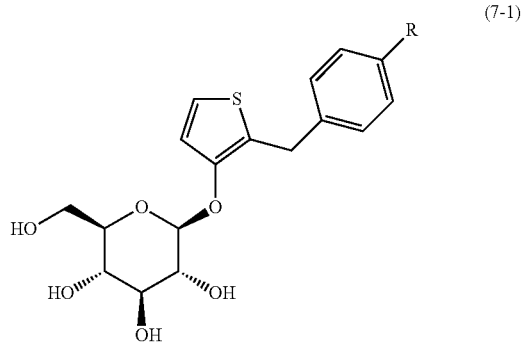

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

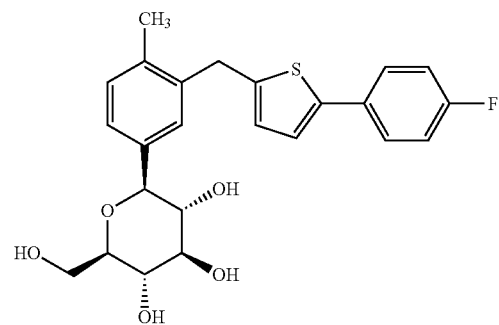 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

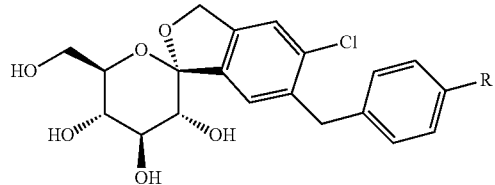

wherein R denotes methoxy, trifluoromethoxy, ethoxy, ethyl, isopropyl or tert. butyl;

(15) a pyrazole-O-glucoside derivative of the formula (15)

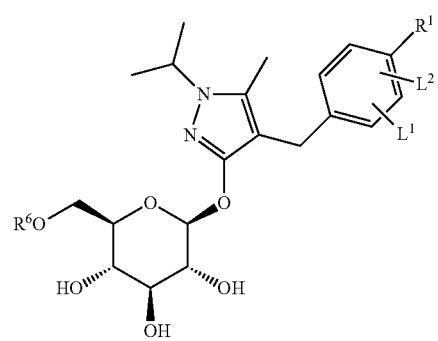

wherein
R¹ denotes $C_1$-alkoxy,
L¹, L² independently of each other denote H or F,
R⁶ denotes H, $(C_{1-3}$-alkyl)carbonyl, $(C_{1-6}$-alkyl)oxycarbonyl, phenyloxycarbonyl, benzyloxycarbonyl or benzylcarbonyl;

(16) Sotagliflozin, represented by formula (16):

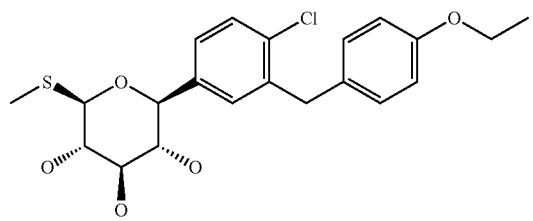

(17) Sergliflozin, represented by formula (17):

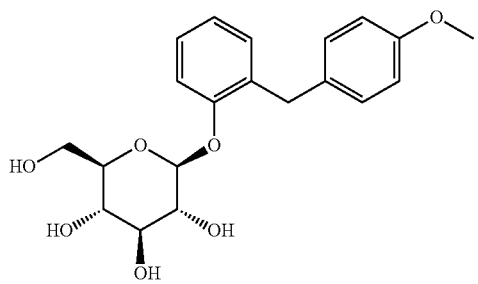 [SMILES: COc1ccc(Cc2ccccc2O[C@@H]2O[C@H](CO)[C@@H](O)[C@H](O)[C@H]2O)cc1]

(18) a compound represented by formula (18):

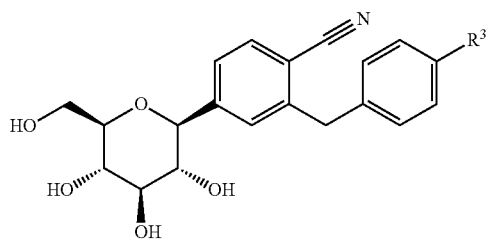

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano; and wherein R³ is preferably selected from cyclopropyl, ethyl, ethinyl, ethoxy, (R)-tetrahydrofuran-3-yloxy or (S)-tetrahydrofuran-3-yloxy; and
R³ most preferably is cyclopropyl,
or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(19) Bexagliflozin, represented by formula (19):

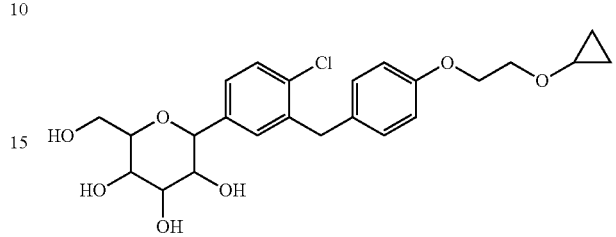

(20) Janagliflozin, represented by formula (20):

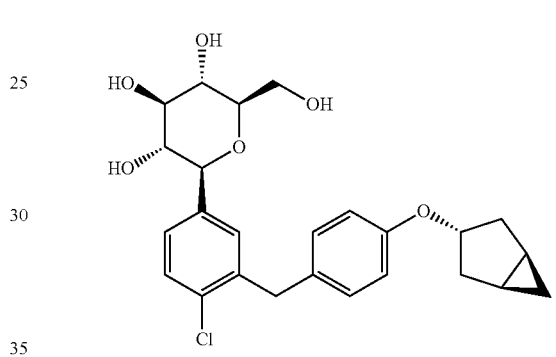

(21) Rongliflozin,
(22) Wanpagliflozin.

The term "velagliflozin" as employed herein refers to velagliflozin of the above structure as well as pharmaceutically acceptable forms thereof, including hydrates and solvates thereof, and crystalline forms thereof. The compound, methods of its synthesis and co-crystals thereof are described in WO 2007/128749, WO 2014/016381 and WO 2019/121509 for example.

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO 2005/092877, WO 2006/120208 and WO 2011/039108 for example. A preferred crystalline form is described in the patent applications WO 2006/117359 and WO 2011/039107 for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example.

The compound of formula (16) above, i.e. sotagliflozin, and its manufacture are described for example in WO 2008/042688 or WO 2009/014970.

Preferred SGLT-2 inhibitors are glucopyranosyl-substituted benzene derivatives. Optionally, one or more hydroxyl groups of the glucopyranosyl group in such one or more SGLT-2 inhibitors may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

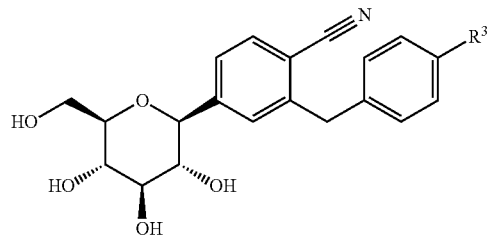

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano; and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Preferably, such SGLT-2 inhibitor is velaglifozin as shown in formula (2). Optionally, one or more hydroxyl groups of the β-D-glucopyranosyl group of velagliflozin may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Thus, in a preferred embodiment, the at least one SGLT-2 inhibitor according to the present invention is a glucopyranosyl-substituted benzene derivative SGLT-2 inhibitor, preferably a SGLT-2 inhibitor of formula (1), more preferably of formula (18), or yet more preferably of formula (2), i.e. velagliflozin, in each case as defined herein above.

Herein, references to SGLT-2 inhibitors and/or their use according to the invention encompass pharmaceutically acceptable forms of the SGLT-2 inhibitors, unless otherwise stated. According to the invention, any pharmaceutically acceptable form of the SGLT-2 inhibitor, e.g. of formula (1), preferably formula (18), more preferably formula (2), may be used. E.g. a crystalline form may be used. Prodrug forms are also encompassed by the present invention.

Prodrug forms may include, e.g., esters and/or hydrates. The term "prodrug" is also meant to include any covalently bonded carrier, which releases the active compound of the invention in vivo when the prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

Crystalline forms for use according to the invention include a complex of an SGLT-2 inhibitor with one or more amino acids (see e.g. WO 2014/016381)—so-called co-crystals. An amino acid for such use may be a natural amino acid. The amino acid may be a proteogenic amino acid (including L-hydroxyproline), or a non-proteogenic amino acid. The amino acid may be a D- or an L-amino acid. In some preferred embodiments, the amino acid is proline (L-proline and/or D-proline, preferably L-proline). E.g., a crystalline complex/co-crystal of velagliflozin with proline (e.g. L-proline) and crystalline water is preferred.

Thus, herein is disclosed a crystalline complex/co-crystal between one or more natural amino acids and an SGLT-2 inhibitor, e.g., a crystalline complex/co-crystal between one or more natural amino acids and a glucopyranosyl-substituted benzene derivative SGLT-2 inhibitor, preferably a SGLT-2 inhibitor of formula (1), more preferably of formula (18) or yet more preferably of formula (2) (velagliflozin).

Furthermore, the availability of a well-defined crystalline form allows the purification of the drug substance by recrystallization.

Apart from the requirements indicated above, it should be generally borne in mind that any change to the solid state of a pharmaceutical composition, which is capable of improving its physical and chemical stability, gives a significant advantage over less stable forms of the same medicament.

A crystalline complex/co-crystal between a natural amino acid and an SGLT-2 inhibitor (e.g. a glucopyranosyl-substituted benzene derivative or a SGLT-2 inhibitor of formula (1), or formula (18) or, particularly, of formula (2), i.e. velaglilfozin) fulfills important requirements mentioned hereinbefore.

SGLT-2 inhibitors for use according to the invention may be prepared as pharmaceutical compositions. They may be prepared as solid or as liquid formulations. In either case, they are preferably prepared for parenteral administration, preferably in liquid form for parenteral administration (see e.g. WO 2017/032799). The SGLT-2 inhibitors may, however, also be prepared, e.g., for oral administration. Solid formulations include tablets, granular forms, and other solid forms such as suppositories. Among solid formulations, tablets and granular forms are preferred.

Pharmaceutical compositions within the meaning of the present invention may comprise an SGLT-2 inhibitor according to the present invention and one or more excipients. Any excipient that allows for, or supports, the intended medical effect may be used. Such excipients are available to the skilled person. Useful excipients are for example anti-adherents (used to reduce the adhesion between the powder (granules) and the punch faces and thus prevent sticking to tablet punches), binders (solution binders or dry binders that hold the ingredients together), coatings (to protect tablet ingredients from deterioration by moisture in the air and make large or unpleasant-tasting tablets easier to swallow), disintegrants (to allow the tablet to break upon dilution), fillers, diluents, flavours, colours, glidants (flow regulators—to promote powder flow by reducing interparticle friction and cohesion), lubricants (to prevent ingredients from clumping together and from sticking to the tablet punches or capsule filling machine), preservatives, sorbents, sweeteners etc.

Formulations according to the invention, e.g. solid formulations, may comprise carriers and/or disintegrants selected from the group of sugars and sugar alcohols, e.g. mannitol, lactose, starch, cellulose, microcrystalline cellulose and cellulose derivatives, e.g. methylcellulose, and the like.

Manufacturing procedures for formulations suitable for ruminants are known to the person skilled in the art, and for solid formulations comprise, e.g., direct compression, dry granulation and wet granulation. In the direct compression process, the active ingredient and all other excipients are placed together in a compression apparatus that is directly applied to press tablets out of this material. The resulting tablets can optionally be coated afterwards in order to protect them physically and/or chemically, e.g. by a material known from the state of the art.

A unit for administration, e.g. a single liquid dose or a unit of a solid formulation, e.g. a tablet, may comprise 0.1 mg to 10 mg, or e.g. 0.3 mg to 1 mg, 1 mg to 3 mg, 3 mg to 10 mg; or 5 to 2500 mg, or e.g. 5 to 2000 mg, 5 mg to 1500 mg, 10 mg to 1500 mg, 10 mg to 1000 mg, or 10-500 mg of an SGLT-2 inhibitor for use according to the invention. As the skilled person would understand, the content of the SGLT-2 inhibitor in a solid formulation, or any formulation as disclosed herein for administration to a ruminant, may be increased or decreased as appropriate in proportion to the body weight of the non-human mammal, preferably ruminant, to be treated.

In one embodiment, a pharmaceutical composition for use according to the invention is designed for oral or parenteral administration, preferably for parenteral administration. Especially the oral administration is ameliorated by excipients, which modify the smell and/or haptic properties of the pharmaceutical composition for the intended patient, e.g. as described.

When the SGLT-2 inhibitor for use according to the invention is formulated for oral administration, it is preferred that excipients confer properties, e.g. palatability and/or chewability that render the formulation suitable for administration to a non-human mammal, preferably ruminant.

Also preferred are liquid formulations. Liquid formulations may be, e.g., solutions, syrups or suspensions. They may be administered directly to the ruminant or may be mixed with the food and/or drink (e.g. drinking water, or the like) of the ruminant. One advantage of a liquid formulation (similar to a formulation in granular form), is that such a dosage form allows precise dosing. For example, the SGLT-2 inhibitor may be dosed precisely in proportion to the body mass of a non-human mammal, preferably ruminant. Typical compositions of liquid formulations are known to the person skilled in the art.

A practitioner skilled in the art can determine suitable doses for the uses of the present invention. Preferred units dosing units include mg/kg bodyweight, i.e. mg SGLT-2 inhibitor per body mass of the non-human mammal, preferably ruminant. An SGLT-2 inhibitor of the present invention may, e.g., be administered in doses of 0.01-10 mg/kg bodyweight per day, e.g. 0.01-5 mg/kg bodyweight per day, e.g. 0.01-4 mg/kg bodyweight per day, e.g. 0.01-3 mg/kg bodyweight per day, e.g. 0.01-2 mg/kg bodyweight per day, e.g. 0.01-1.5 mg/kg bodyweight per day, e.g., 0.01-1 mg/kg bodyweight per day, e.g. 0.01-0.75 mg/kg bodyweight per day, e.g. 0.01-0.5 mg/kg bodyweight per day, e.g. 0.01-0.4 mg/kg bodyweight per day; or 0.03 to 3.0 mg/kg bodyweight per day, preferably from 0.02 to 2.0 mg/kg bodyweight per day, more preferably from 0.01 to 1 mg/kg bodyweight per day. In another preferred embodiment, the dose is 0.03 mg/kg bodyweight or 0.3 mg/kg bodyweight or 3 mg/kg bodyweight. A practitioner skilled in the art is able to prepare an SGLT-2 inhibitor of the invention for administration according to a desired dose.

EXAMPLES

The following examples serve to further illustrate the present invention; but the same should not be construed as a limitation of the scope of the invention disclosed herein.

Example 1 Pharmacokinetics (PK)/Pharmacodynamics (PD) and Milk Reduction by a Single Velagliflozin Dosing in Lactating Cows Velagliflozin treatment is tested in n=4 lactating Holstein-Frisian cows. In weekly intervals, velagliflozin is administered intravenously (i.v.) in increasing doses (0.03 mg/kg bodyweight-0.3 mg/kg bodyweight-3 mg/kg bodyweight) in the morning after AM (ante meridian) milking into the right jugular vein in a volume of 2.5 ml of a propylene glycol based solution per 100 kg body weight. Blood samples for determination of velagliflozin plasma levels and urine samples for determination of glucose and creatinine levels are collected one day prior to treatment and ~8 hours, ~24 hours and ~48 hours post treatment and stored frozen until being analysed. Blood glucose and ketone body (beta-hydroxy-butyrate) concentrations are determined immediately after blood collection at the same time points. The total urinary creatinine excreted per day is rather constant in mammals, thus, since urine volume was not determined, the glucose to creatinine ratio was calculated as a surrogate of the total glucose excretion. All animals are milked twice daily, in the morning (ante meridian—AM) and in the late afternoon (post meridian—PM). Throughout the study, milk yield is recorded as kg per animal per milking.

Figure 1:
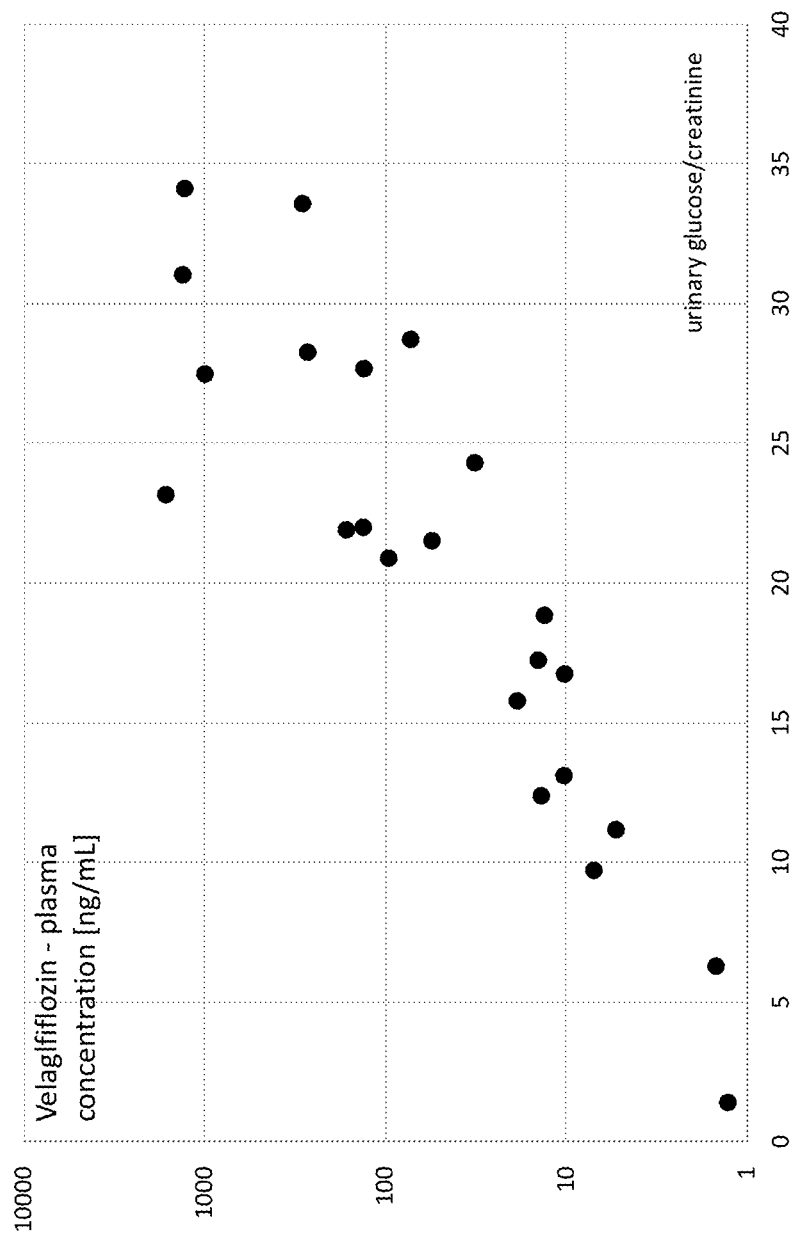
FIG. 1 shows the correlation between velagliflozin plasma concentrations and urinary glucose excretion normalized to urinary creatinine (glucose/creatinine) in Holstein-Frisian cows.
Figure 2:
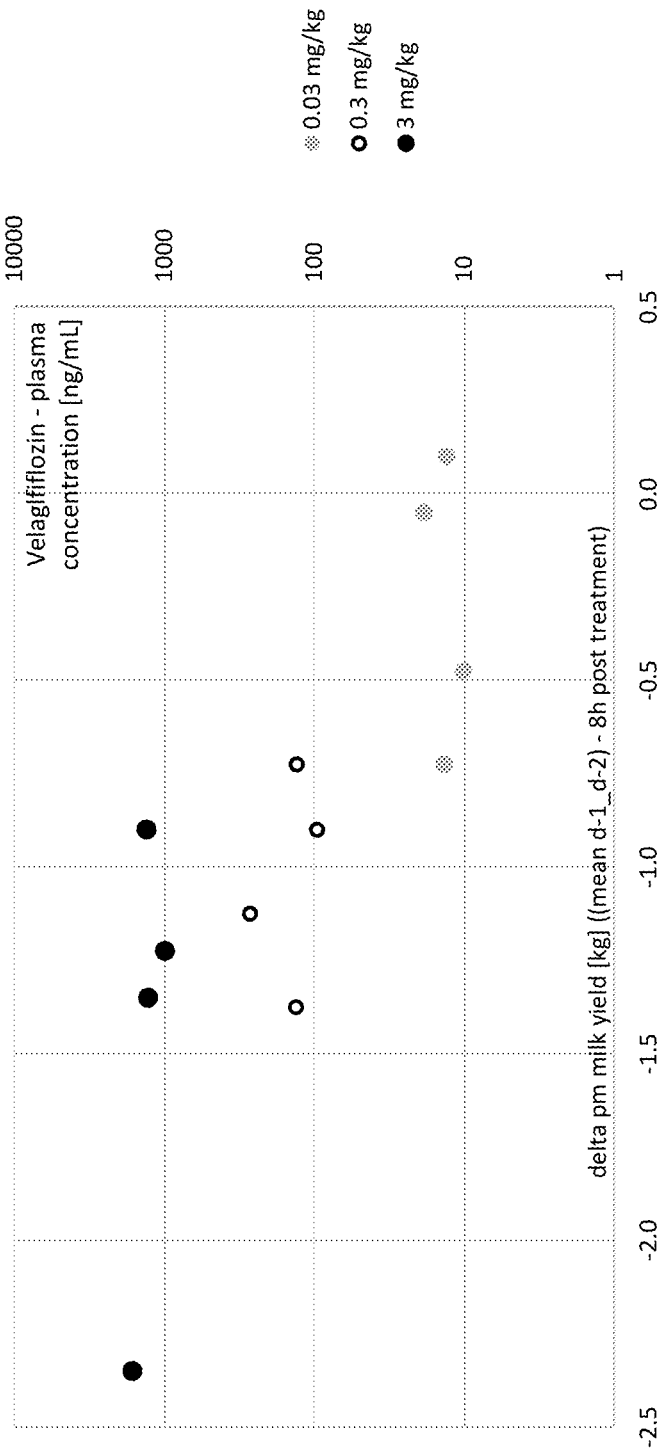
FIG. 2 depicts the delta values (kg) between mean afternoon (post meridian—PM) milking of two days before administration of velagliflozin and milk yield (individual values) about 8 hours after i.v. administration (PM milking) of three different doses of velagliflozin (0.03 mg/kg bodyweight; 0.3 mg/kg bodyweight and 3 mg/kg bodyweight) in dairy cows. It further depicts the correlation between reduction of milk yield and velagliflozin plasma concentrations 8 hours after treatment in Holstein-Frisian cows.

Results:
Velagliflozin plasma level show a linear dose to exposure relationship (see FIG. 1).
The urinary glucose excretion normalized to urinary creatinine increases in a dose/exposure dependent manner (FIG. 1).
After treatment, the milk yield of the subsequent milking (PM) decreases in a dose/exposure dependent manner (FIG. 2).
Of safety relevance, blood glucose or ketone body level were within normal reference ranges after treatment with all dosages of velagliflozin.
Clearly, these effects are dependent on the plasma velagliflozin level, indicating that also other parenteral administration routes—e.g. intramuscular or subcutaneous administrations are effective. It is thus concluded that a single (e.g. parenteral) dose of at least one SGLT-2 inhibitor, such as velagliflozin, can be safely employed in lactating cows to reduce milk yield.

Example 2 Reduction of Milk Production and Udder Engorgement

In studies in lactating cows, SGLT-2 inhibitor, such as velaglifozin, treatment can be performed as a single parenteral administration, preferably s.c. or i.m. or also as two treatments e.g. ~24 h or 48 h apart.

The treatment is also performed in combination with or subsequently to treatment with feed supplements, e.g. Bovikalc® Dry, and/or a reduction in feed offered to the cow with the aim to reduce the milk production prior to dry-off.

Reduction in milk yield is evaluated by weighing of the milk yield per animal and per milking (see e.g. Example 1).

Udder engorgement is evaluated by measuring the teat distance, by direct pressure measurements and/or measuring udder firmness—indicative for engorgement using for instance a dynamometer (e.g. Penefel DFT 14; Agro Technologies, Forges-les-Eaux, France). These readings are compared between measurements before the last milking with those on the following days after dry-off. However, also treatment effects on reduction in milk yield and udder engorgement can be compared between cows treated with at least one SGLT-2 inhibitor with cows that receive no treatment or cows offered a reduced feed ration only.

Example 3 Effects on Milk Composition and Involution Marker

In studies as described in Example 2, concurrent with the reduction in milk yield changes in the composition of the milk/secreted fluid, indicating the involution of the secretory cells and/or the disruption of cellular tight junctions are investigated. For instance, somatic cell counts, bovine serum albumin, lactose, potassium and sodium as well as total protein, whey protein, casein protein, protease peptone, lactoferrin level and/or the gelatinase activity are measured.

To achieve this, small amounts of mammary secretions (5 to 50 mL) are collected from alternating quarters on several days after the last milking, i.e. dry-off.

These readings are compared with measurements before the last milking compared with those on the following days after dry-off; but also treatment effects may be compared between cows treated with at least one SGLT-2 inhibitor, e.g. velagliflozin, with cows that receive no treatment or cows offered a reduced feed ration only.

Example 4 Reduction of Milk Leakage and Intra-Mammary Infections (IMI) During Dry Period In studies as described in Example 2, also in the first days after dry-off leakage of milk from the mammary gland, i.e. milk dropping or flowing from any teat is evaluated. In addition, the udder quarter can be closely monitored to detect symptoms of intra-mammary infections or mastitis, i.e. warm or hot, sensitive or swollen udder quarters. Besides, symptoms of systemic illness, e.g. signs of fever, rapid pulse, depression, weakness and loss of appetite may be present. Also, small amounts of mammary secretions (5 to 50 mL) are collected from alternating quarters on several days after the last milking, i.e. dry-off to investigate eventual subclinical intra-mammary infections/presence of microorganisms.

These readings are compared between cows treated with at least one SGLT-2 inhibitor, such as velagliflozin, with cows that receive no treatment or cows offered a reduced feed ration only.

Example 5 Reduction of Discomfort and Stress Caused by Dry-Off

In studies in pregnant, lactating cows, SGLT-2 inhibitor treatment, for instance by means of velagliflozin, is installed typically e.g. in the eighth month of gestation at dry-off. The treatment is also performed in combination with or subsequently to treatment with feed supplements, e.g. Bovikalc® Dry, and/or a reduction in feed offered to the cow with the aim to reduce the milk production prior to dry-off.

Stress and/or other discomfort measurements after dry-off are evaluated recording the time spent lying and/or ruminating. In addition, the increase in the concentration of blood cortisol or faecal glucocorticoid metabolites is measured.

An udder pain score can be employed, i.e. the behaviour of the cows may be classified into 4 categories (0=no udder pain; 1=light udder pain; 2=moderate udder pain and 3=severe udder pain) depending on their reaction at udder palpation (from no behavioural response to refusal of the palpation).

These readings are compared between cows treated with at least one SGLT-2 inhibitor, such as velagliflozin, with cows that receive no treatment or cows offered a reduced feed ration only.

Example 6 Treatment in Ruminants at Dry-Off—Safety and Long Term Effects

In studies in pregnant, lactating cows, treatment with at least one SGLT-2 inhibitor, such as velagliflozin, can be installed typically e.g. in the eighth month of gestation at dry-off. The treatment is performed as a single administration or also as two treatments ~24 h or 48 h apart after last milking. The treatment is also performed in combination with or subsequently to treatment with feed supplements, e.g. Bovikalc® Dry, and/or a reduction in feed offered to the cow with the aim to reduce the milk production prior to dry-off.

The safety of a for instance velagliflozin treatment can be assessed by evaluating the metabolic response of the negative energy balance induced, i.e. evaluating the blood glucose and ketone body, as well as the blood lipid concentrations (e.g. NEFAs). In addition, the electrolyte balance of the cows is monitored, with e.g. special emphasise on the calcium homeostasis.

The administration of at least one SGLT-2 inhibitor, such as velagliflozin, even makes it possible to improve the immune status and/or liver function of dairy cows. This can be measured by markers of a systemic proinflammatory status, e.g. acute phase proteins like serum amyloid A (SAA) or haptoglobulin.

Besides, the impact on the foetus or even abortive effects can be monitored.

Severity and incidence of safety relevant observations are compared between SGLT-2 inhibitor (e.g. velagliflozin) treated cows with cows that receive no treatment or cows offered a reduced feed ration. In addition, a combined treatment with the SGLT-2 inhibitor, e.g. velagliflozin, and offering reduced feed ratios shows that there is no adverse influence of the SGLT-2 inhibitor, e.g. velagliflozin, treatment at dry-off on the safety of a pregnant cow and the foetus.

In studies where the subsequent lactation is monitored it can be shown that treatment with at least one SGLT-2 inhibitor, such as velagliflozin, does not negatively affect reproduction/fertility and/or milk yield and/or quality of milk in the next lactation. In contrast, it can even reduce the incidence of new intra-mammary infections or mastitis in the first month after start of the next lactation.

These readings are compared between cows treated with at least one SGLT-2 inhibitor, such as velagliflozin, with cows that receive no treatment or cows offered a reduced feed ration only prior to dry-off.

Example 7 Dose/Pharmacodynamics (PD) of Dapagliflozin after a Single Parenteral Injection in Lactating Ruminants In studies in pregnant or non-pregnant, lactating cows, treatment with dapagliflozin is performed as described in Example 1. I.e. employing a dose escalation design the cows receive a single parenteral injection containing dapagliflozin in weekly intervals. Urinary glucose and creatinine, blood glucose and ketone body concentration and milk yield are measured. Pharmacodynamics data are evaluated as described in Example 1. Thus, it is investigated:

If the urinary glucose excretion normalized to urinary creatinine increases in a dose/exposure dependent manner.

That, after treatment, the milk yield of the subsequent milking (PM) decreases in a dose/exposure dependent manner.

And also, if blood glucose or ketone body level stay within normal reference ranges after treatment with all dosages.

Thus, similar to what is described with velagliflozin, also for dapagliflozin it is anticipated that a parenteral treatment at a dose between 0.01 to 10 mg/kg bodyweight per injection has the potential to be safely employed in lactating cows to reduce milk yield and have beneficial effects if treatment is installed at dry-off in analogy to Examples 2 to 6 of the present invention.

Example 8 Dose/Pharmacodynamics (PD) of Canagliflozin after a Single Parenteral Injection in Lactating Ruminants In studies in pregnant or non-pregnant, lactating cows, treatment with canagliflozin is performed as described in Example 1. I.e. employing a dose escalation design the cows receive a single parenteral injection containing canagliflozin in weekly intervals. Urinary glucose and creatinine, blood glucose and ketone body concentration and milk yield are measured. Pharmacodynamic data are evaluated as described in Example 1. Thus, it is investigated:

If the urinary glucose excretion normalized to urinary creatinine increases in a dose/exposure dependent manner.

That, after treatment, the milk yield of the subsequent milking (PM) decreases in a dose/exposure dependent manner.

And also, if blood glucose or ketone body level stay within normal reference ranges after treatment with all dosages.

Thus, similar to what is described with velagliflozin, also for canagliflozin it is anticipated that a parenteral treatment at a dose between 0.01 to 10 mg/kg bodyweight per injection has the potential to be safely employed in lactating cows to reduce milk yield and have beneficial effects if treatment is installed at dry-off in analogy to Examples 2 to 6 of the present invention.

Example 9 Dose/Pharmacodynamics (PD) of Empagliflozin after a Single Parenteral Injection in Lactating Ruminants In studies in pregnant or non-pregnant, lactating cows, treatment with empagliflozin is performed as described in Example 1. I.e. employing a dose escalation design the cows receive a single parenteral injection containing empagliflozin in weekly intervals. Urinary glucose and creatinine, blood glucose and ketone body concentration and milk yield are measured. Pharmacodynamic data are evaluated as described in Example 1. Thus, it is investigated:

If the urinary glucose excretion normalized to urinary creatinine increases in a dose/exposure dependent manner.

That, after treatment, the milk yield of the subsequent milking (PM) decreases in a dose/exposure dependent manner.

And also, if blood glucose or ketone body level stay within normal reference ranges after treatment with all dosages.

Thus, similar to what is described with velagliflozin, also for empagliflozin it is anticipated that a parenteral treatment at a dose between 0.01 to 10 mg/kg bodyweight per injection has the potential to be safely employed in lactating cows to reduce milk yield and have beneficial effects if treatment is installed at dry-off in analogy to Examples 2 to 6 of the present invention.

Example 10 Dose/Pharmacodynamics (PD) of Ertugliflozin after a Single Parenteral Injection in Lactating Ruminants In studies in pregnant or non-pregnant, lactating cows, treatment with ertugliflozin is performed as described in Example 1. I.e. employing a dose escalation design the cows receive a single parenteral injection containing ertugliflozin in weekly intervals. Urinary glucose and creatinine, blood glucose and ketone body concentration and milk yield are measured. Pharmacodynamic data are evaluated as described in Example 1. Thus, it is investigated:

If the urinary glucose excretion normalized to urinary creatinine increases in a dose/exposure dependent manner.

That, after treatment, the milk yield of the subsequent milking (PM) decreases in a dose/exposure dependent manner.

And also, if blood glucose or ketone body level stay within normal reference ranges after treatment with all dosages.

Thus, similar to what is described with velagliflozin, also for ertugliflozin it is anticipated that a parenteral treatment at a dose between 0.01 to 10 mg/kg bodyweight per injection has the potential to be safely employed in lactating cows to reduce milk yield and have beneficial effects if treatment is installed at dry-off in analogy to Examples 2 to 6 of the present invention.

Example 11 Effects on Milk Composition and Involution Marker—Ex Vivo/In Vitro Assessment The direct effects of SGLT2 inhibition on the bovine mammary gland are studied in isolated perfused bovine udders as well as in (primary) bovine mammary epithelial cells (MECs).

The beneficial effects on the bovine mammary gland for dry-off are shown e.g. in the milk like secretion of perfused udders and/or the supernatant in MEC cultures—the reduction of lactose and/or triglycerides are measured. Also, the reduction of markers of milk production like beta-casein is quantified, e.g. by determining the protein content in western blots of cell lysates.

In addition, the expression of involution marker are assessed. The exposure of perfused bovine udders and/or bovine MECs with at least one SGLT2 inhibitor according to the present invention influences apoptosis and/or autophagy. These effects are measured, e.g. by quantifying the expression of markers like transforming growth factor-beta1 and/or sequestosome-1 (also known as p62).

Example 12 Dose/Pharmacodynamics (PD) of Velagliflozin after a Single Administration in Lactating Laboratory Animals In studies in lactating laboratory animals, such as dogs, cats, rats, mice and/or rabbits, treatment with velagliflozin is performed similar as described in Example 1. I.e. employing a dose escalation design the animals receive a single parenteral injection or, alternatively, oral dosages containing velagliflozin in weekly intervals. Urinary glucose and creatinine, blood glucose and ketone body concentration and milk yield are measured. In laboratory animals, the milk yield is measured using a weigh-suckle-weigh method. Briefly, the mother is separated from her pups for e.g. 3 h. Then the pups are weighed, allowed to suckle for e.g. 1 h, and are weighed again. This procedure may be repeated several times per day, e.g. the day before and the day of treatment with velagliflozin.

Pharmacodynamic read outs investigated are e.g.:

If the urinary glucose excretion normalized to urinary creatinine increases in a dose/exposure dependent manner.

That, after treatment, the milk yield of the subsequent milking decreases in a dose/exposure dependent manner.

And also, if blood glucose or ketone body level stay within normal reference ranges after treatment with all dosages.

These readings are compared between, before, or after treatment with velagliflozin, or between animals that are treated with velagliflozin compared to others, that receive no treatment or placebo treatment.

The dose depended reduction of milk secretion of velagliflozin in cows (see Example 1) and laboratory animals indicate that SGLT2 inhibitors, like velagliflozin, but also others can successfully treat any condition of an animal (preferably ruminants, dogs, cats, horses, pigs) that is associated with an unwanted lactation—e.g. dry-off in dairy ruminants (Example 1), pseudopregnancy/galactorrhea in animals (Example 17). But also, if for other reasons it is required that whelping is to be discontinued abruptly, the treatment with at least one SGLT2 inhibitor according to the present invention is anticipated to reduce the milk secretion and in addition successfully reduce and/or prevent associated clinical signs—e.g. mammary engorgement, pain, milk leakage and/or mastitis.

Example 13 Dose/Pharmacodynamics (PD) of Dapagliflozin after a Single Administration in Lactating Laboratory Animals In studies in lactating laboratory animals, such as dogs, cats, rats, mice and/or rabbits, treatment with dapagliflozin is performed similar as described in Example 1. I.e. employing a dose escalation design the animals receive a single parenteral injection or, alternatively, oral dosages containing dapagliflozin in weekly intervals. Urinary glucose and creatinine, blood glucose and ketone body concentration and milk yield are measured. In laboratory animals, the milk yield is measured using a weigh-suckle-weigh method. Briefly, the mother is separated from her pups for e.g. 3 h. Then the pups are weighed, allowed to suckle for e.g. 1 h, and are weighed again. This procedure may be repeated several times per day, e.g. the day before and the day of treatment with dapagliflozin. Pharmacodynamic read outs investigated are e.g.:

- If the urinary glucose excretion normalized to urinary creatinine increases in a dose/exposure dependent manner.
- That, after treatment, the milk yield of the subsequent milking decreases in a dose/exposure dependent manner.
- And also, if blood glucose or ketone body level stay within normal reference ranges after treatment with all dosages.

These readings are compared between, before, or after treatment with dapagliflozin, or between animals that are treated with dapagliflozin compared to others, that receive no treatment or placebo treatment.

Example 14 Dose/Pharmacodynamics (PD) of Canagliflozin after a Single Administration in Lactating Laboratory Animals In studies in lactating laboratory animals, such as dogs, cats, rats, mice and/or rabbits, treatment with canagliflozin is performed similar as described in Example 1. I.e. employing a dose escalation design the animals receive a single parenteral injection or, alternatively, oral dosages containing canagliflozin in weekly intervals. Urinary glucose and creatinine, blood glucose and ketone body concentration and milk yield are measured. In laboratory animals, the milk yield is measured using a weigh-suckle-weigh method. Briefly, the mother is separated from her pups for e.g. 3 h. Then the pups are weighed, allowed to suckle for e.g. 1 h, and are weighed again. This procedure may be repeated several times per day, e.g. the day before and the day of treatment with canagliflozin. Pharmacodynamic read outs investigated are e.g.:

- If the urinary glucose excretion normalized to urinary creatinine increases in a dose/exposure dependent manner.
- That, after treatment, the milk yield of the subsequent milking decreases in a dose/exposure dependent manner.
- And also, if blood glucose or ketone body level stay within normal reference ranges after treatment with all dosages.

These readings are compared between, before, or after treatment with canagliflozin, or between animals that are treated with canagliflozin compared to others, that receive no treatment or placebo treatment.

Example 15 Dose/Pharmacodynamics (PD) of Empagliflozin after a Single Administration in Lactating Laboratory Animals In studies in lactating laboratory animals, such as dogs, cats, rats, mice and/or rabbits, treatment with empagliflozin is performed similar as described in Example 1. I.e. employing a dose escalation design the animals receive a single parenteral injection or, alternatively, oral dosages containing empagliflozin in weekly intervals. Urinary glucose and creatinine, blood glucose and ketone body concentration and milk yield are measured. In laboratory animals, the milk yield is measured using a weigh-suckle-weigh method. Briefly, the mother is separated from her pups for e.g. 3 h. Then the pups are weighed, allowed to suckle for e.g. 1 h, and are weighed again. This procedure may be repeated several times per day, e.g. the day before and the day of treatment with empagliflozin. Pharmacodynamic read outs investigated are e.g.:

- If the urinary glucose excretion normalized to urinary creatinine increases in a dose/exposure dependent manner.
- That, after treatment, the milk yield of the subsequent milking decreases in a dose/exposure dependent manner.
- And also, if blood glucose or ketone body level stay within normal reference ranges after treatment with all dosages.

These readings are compared between, before, or after treatment with empagliflozin, or between animals that are treated with empagliflozin compared to others, that receive no treatment or placebo treatment.

Example 16 Dose/Pharmacodynamics (PD) of Ertugliflozin after a Single Administration in Lactating Laboratory Animals In studies in lactating laboratory animals, such as dogs, cats, rats, mice and/or rabbits, treatment with ertugliflozin is performed similar as described in Example 1. I.e. employing a dose escalation design the animals receive a single parenteral injection or, alternatively, oral dosages containing ertugliflozin in weekly intervals. Urinary glucose and creatinine, blood glucose and ketone body concentration and milk yield are measured. In laboratory animals, the milk yield is measured using a weigh-suckle-weigh method. Briefly, the mother is separated from her pups for e.g. 3 h. Then the pups are weighed, allowed to suckle for e.g. 1 h, and are weighed again. This procedure may be repeated several times per day, e.g. the day before and the day of treatment with ertugliflozin. Pharmacodynamic read outs investigated are e.g.:

- If the urinary glucose excretion normalized to urinary creatinine increases in a dose/exposure dependent manner.
- That, after treatment, the milk yield of the subsequent milking decreases in a dose/exposure dependent manner.
- And also, if blood glucose or ketone body level stay within normal reference ranges after treatment with all dosages.

These readings are compared between, before, or after treatment with ertugliflozin, or between animals that are treated with ertugliflozin compared to others, that receive no treatment or placebo treatment.

Example 17 Treatment with SGLT2 Inhibitors for the Reduction of Milk Secretion in Cases of Unwanted Lactation Incl. e.g. Galactorrhea and/or Pseudopregnancy The previous examples have described, that the administration of at least one SGLT2 inhibitor according to the present invention can successfully treat any condition of an animal (preferably ruminant, dog, cat, horse, and/or pig) that is associated with an unwanted lactation—e.g. dry-off in dairy ruminants (Example 1). Also, other clinical conditions are often associated with an unwanted lactation, mammary engorgement and/or milk leakage. E.g. this is encountered in dogs affected by pseudopregnancy and/or galactorrhea.

In affected dogs, SGLT-2 inhibitor, such as velaglifozin, treatment can be performed as a parenteral administration, preferably s.c. or i.m. or also by oral administration. The treatment may be a single treatment or repeated daily treatments e.g. ~24 h or 48 h apart until the symptoms resolve.

Responses to treatment are evaluated by visual inspection of the mammary gland area—i.e. engorgement and/or milk leakage—and/or manual palpation to evaluate pain and/or evolving intra mammary inflammation. Also, the resolution of additional behavioural symptoms (e.g. depression, weight gain, vomiting, or appetite loss) may be evaluated. The read outs may be reported on owner questionnaires.

REFERENCES (1) Bertulat S et al., J Dairy Sci 2017, 100(4): 3220-3232
(2) EP 2 349 272
(3) EP 2 675 527
(4) Gross J J et al., J Anim Physiol Anim Nutr 2015, 99: 747-756
(5) Lanctôt S et al., J Dairy Sci 2017, 100(3): 2269-2281
(6) Maynou G et al., J Dairy Sci 2018, 101(12): 1-12
(7) US 2004/0258778
(8) US 2011/0245261
(9) US 2014/0024670
(10) U.S. Pat. No. 4,412,993
(11) U.S. Pat. No. 6,391,849
(12) U.S. Pat. No. 8,133,916
(13) U.S. Pat. No. 9,487,557
(14) U.S. Pat. No. 9,744,158
(15) WO 2004/113378
(16) WO 2007/128749
(17) WO 2009/143020
(18) WO2014/016381
(19) WO 2015/173584
(20) WO 2016/104643
(21) WO 2017/156632
(22) WO 2019/121509
(23) Zhao F Q et al., J. Dairy Sci., 2005, 88: 2738-2748
(24) Zhao F Q, J Mammary Gland Biol Neoplasia 2014, 19: 3-17

The following clauses are also comprised by the present invention:

1. Use of at least one SGLT-2 inhibitor in ruminants, preferably for drying-off of ruminants.
2. Method of improving and/or facilitating the drying-off of ruminants comprising administering to such ruminants at least one SGLT-2 inhibitor.
3. Method of reducing the milk production in pregnant and/or lactating ruminants comprising administering to such ruminants at least one SGLT-2 inhibitor.
4. Method of decreasing milk accumulation and/or engorgement in the udder of ruminants comprising administering to such ruminants at least one SGLT-2 inhibitor.
5. Method of decreasing the discomfort associated with udder engorgement, such as increasing the daily lying time and/or reduction of stress, of ruminants comprising administering to such ruminants at least one SGLT-2 inhibitor.
6. Method of decreasing milk leakage after drying-off of ruminants comprising administering to such ruminants at least one SGLT-2 inhibitor.
7. Method of decreasing the incidence of intra-mammary infections (IMI), preferably mastitis and/or metritis, in ruminants comprising administering to such ruminants at least one SGLT-2 inhibitor.
8. The use or method according to any one of clauses 1 to 7, wherein the at least one SGLT-2 inhibitor is administered in a therapeutically effective amount without exerting any harmful and/or abortifacient effects on pregnant ruminants and/or wherein the at least one SGLT-2 inhibitor is administered in a therapeutically effective amount without exerting any negative effects on the subsequent reproduction cycle/fertility and milk yield and/or milk quality in the next lactation.
9. The use or method according to clause 8, wherein the at least one SGLT-2 inhibitor is administered in a therapeutically effective amount that additionally or alternatively effects a reduction of the incidence of new intra-mammary infections (IMI) or mastitis in the first month after start of the next lactation.
10. The use or method according to any one of clauses 1 to 9, wherein the at least one SGLT-2 inhibitor is selected from the group consisting of:
   (1) a glucopyranosyl-substituted benzene derivative of the formula (1)

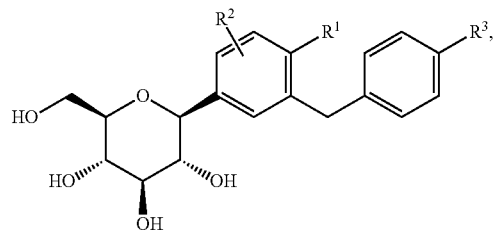

wherein $R^1$ denotes cyano, Cl or methyl (most preferably cyano);
$R^2$ denotes H, methyl, methoxy or hydroxy (most preferably H) and
$R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methylsulfonyl, ethylsulfinyl, ethylsulfonyl, trimethylsilyl, (R)-tetrahydrofuran-3-yloxy or (S)-tetrahydrofuran-3-yloxy or cyano;
wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

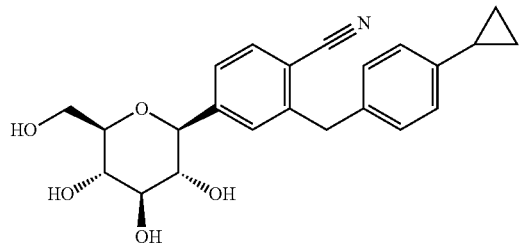 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

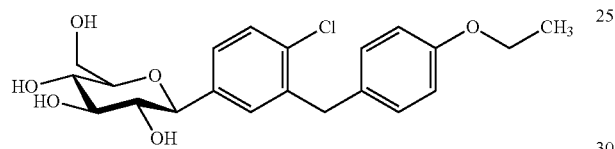

(4) Canagliflozin, represented by formula (4):

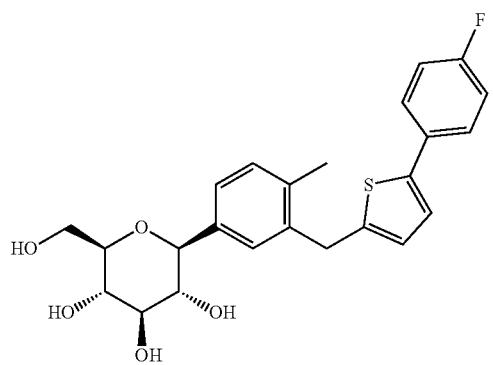 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (6):

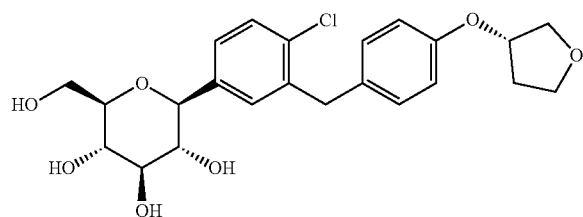 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

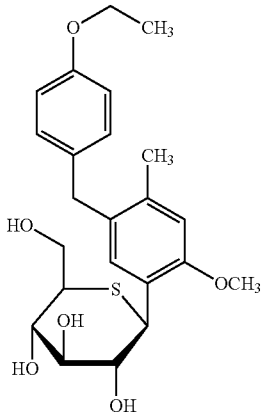

(7) Tofogliflozin, represented by formula (7):

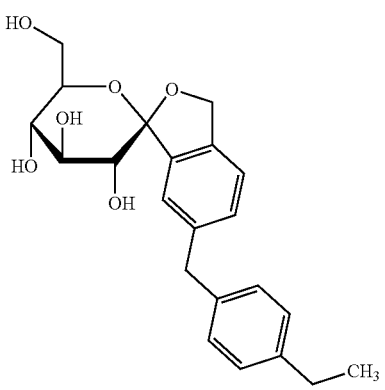

(8) Ipragliflozin, represented by formula (8):

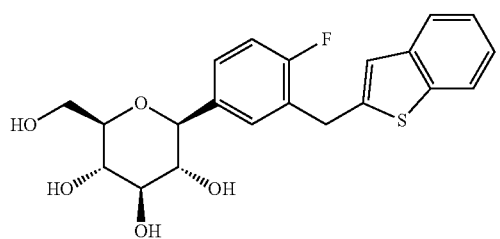 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

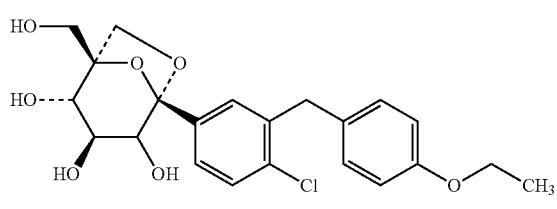

(10) Atigliflozin, represented by formula (10):

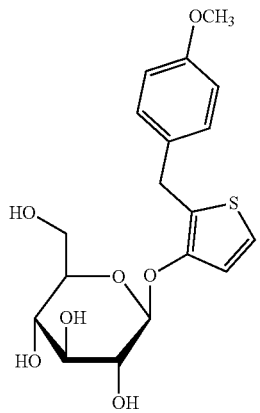

(11) Remogliflozin, represented by formula (11):

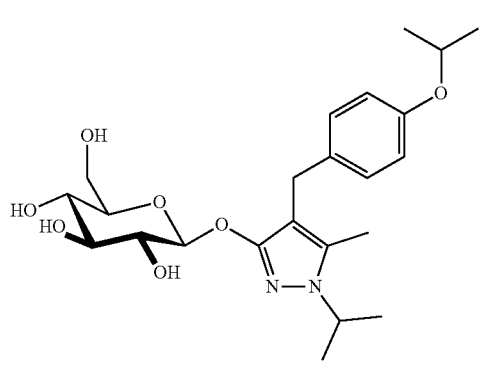

(11A) Remogliflozin etabonate, represented by formula (11A):

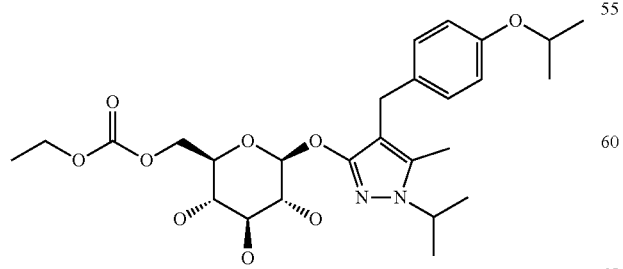

(12) a thiophene derivative of the formula (12)

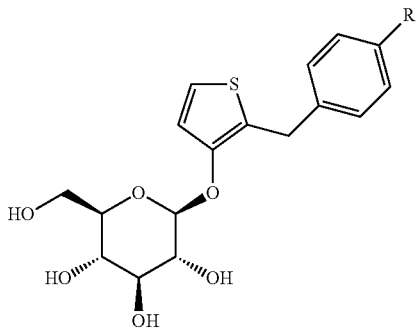

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

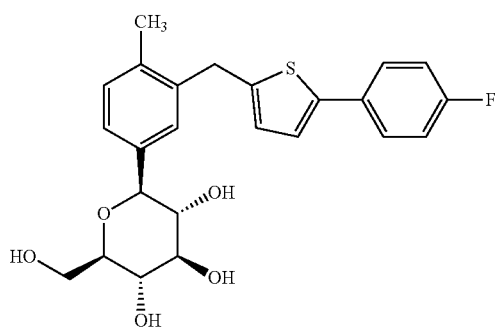 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

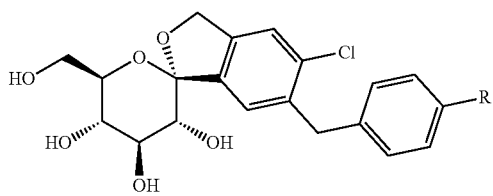

wherein R denotes methoxy, trifluoromethoxy, ethoxy, ethyl, isopropyl or tert. butyl;

(15) a pyrazole-O-glucoside derivative of the formula (15)

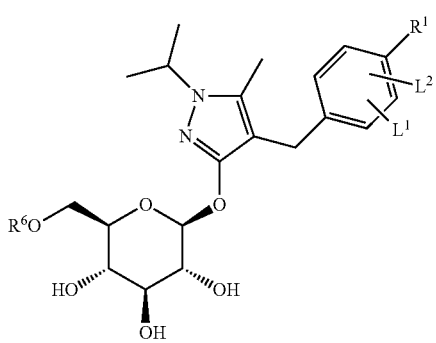

wherein
$R^1$ denotes $C_{1-3}$-alkoxy,
$L^1$, $L^2$ independently of each other denote H or F,
$R^6$ denotes H, $(C_{1-3}$-alkyl)carbonyl, $(C_{1-6}$-alkyl)oxycarbonyl, phenyloxycarbonyl, benzyloxycarbonyl or benzylcarbonyl;

(16) Sotagliflozin, represented by formula (16):

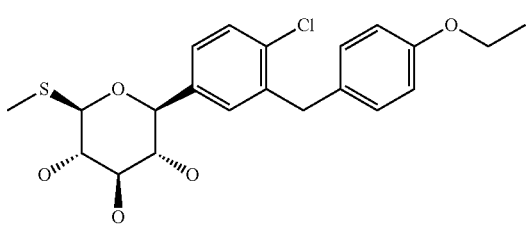 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

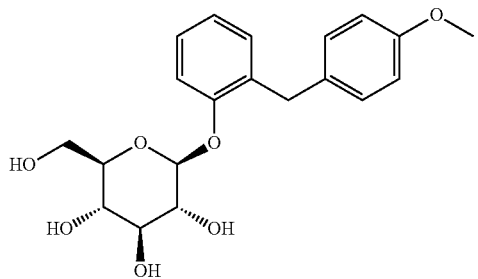 [SMILES: COc1ccc(Cc2ccccc2O[C@@H]2O[C@H](CO)[C@@H](O)[C@H](O)[C@H]2O)cc1]

(18) a compound represented by formula (18):

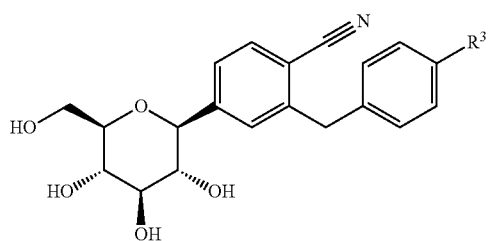

wherein
$R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-}$-alkyl)-carbonyl;

(19) Bexagliflozin, represented by formula (19):

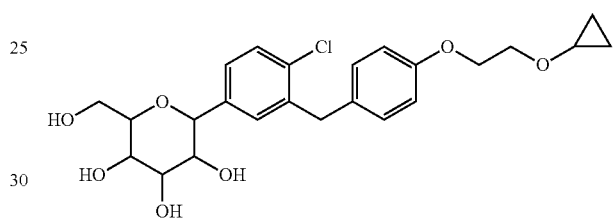

(20) Janagliflozin, represented by formula (20):

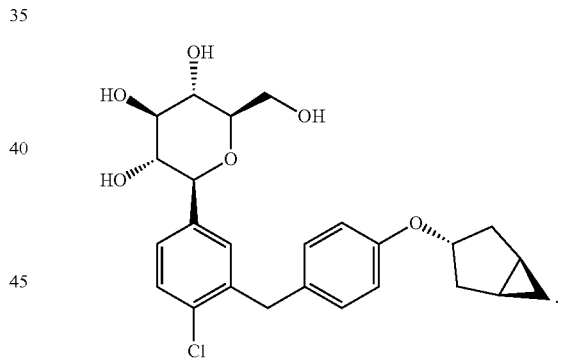

11. The use or method according to any one of clauses 1 to 10, wherein the ruminants are selected from the group consisting of: bovine, caprine, ovine; more preferably selected from the group consisting of: cattle, cows, goats, sheep; even more preferably selected from the group consisting of: dairy cattle, pregnant and/or lactating dairy cattle; most preferably selected from the group consisting of: cows, pregnant and/or lactating cows.

12. The use or method according to any one of clauses 1 to 11, wherein the at least one SGLT-2 inhibitor is administered orally, parenterally, rectally, intravaginally, intravenously, subcutaneously or intramuscularly, preferably subcutaneously, intramuscularly or intravenously.

13. The use or method according to any one of clauses 1 to 12, wherein the at least one SGLT-2 inhibitor is administered at a dose of 0.01 mg/kg bodyweight to 10 mg/kg bodyweight, preferably at a dose of 0.01 mg/kg bodyweight to 5 mg/kg bodyweight, more preferably at a dose of 0.01 mg/kg bodyweight to 3 mg/kg bodyweight, even more preferably at a dose of 0.03 mg/kg bodyweight to 3 mg/kg bodyweight, most preferably at a dose of 0.03 mg/kg bodyweight or 0.3 mg/kg bodyweight or 3 mg/kg bodyweight.

14. The use or method according to any one of clauses 1 to 13, wherein the at least one SGLT-2 inhibitor is administered once, twice, three-times, four-times, five-times, six-times or daily for a week, preferably once only at start of drying-off or twice as two treatments 24 hours or 48 hours apart after last milking.

15. The use or method according to any one of clauses 1 to 14, wherein the at least one SGLT-2 inhibitor is velagliflozin and velagliflozin is administered as single SGLT-2 inhibitor, preferably subcutaneously or intramuscularly, once only at start of drying-off or twice (24 h or 48 h apart) at a dose of 0.03 mg/kg bodyweight to 3 mg/kg bodyweight, preferably at a dose of 0.03 mg/kg bodyweight or 0.3 mg/kg bodyweight or 3 mg/kg bodyweight.

16. The use or method according to any one of clauses 1 to 15, wherein the at least one SGLT-2 inhibitor is administered before, after or concomitantly with administering at least one feed supplement, such as Bovikalc® Dry, to the ruminant and/or before, after or concomitantly with a reduction in feed offered to the ruminant.

17. The use or method according to clause 16, wherein the feed supplement comprises one or more acidifying agents selected from the group consisting of: ammonium chloride, calcium chloride and/or calcium sulfate, more preferably comprises ammonium chloride and calcium chloride and calcium sulfate, even more preferably comprises 5% (w/w) to 15% (w/w) ammonium chloride and 40% (w/w) to 60% (w/w) calcium chloride and 15% (w/w) to 25% (w/w) calcium sulfate, most preferably comprises 10.4% (w/w) ammonium chloride and 51.9% (w/w) calcium chloride and 20.1% (w/w) calcium sulfate.

The invention claimed is:

1. A method of improving and/or facilitating the drying-off of a non-human mammal, comprising administering to the non-human mammal at least one SGLT2 inhibitor, wherein the at least one SGLT-2 inhibitor is selected from the group consisting of:
   (1) a glucopyranosyl-substituted benzene derivative of the formula (1)

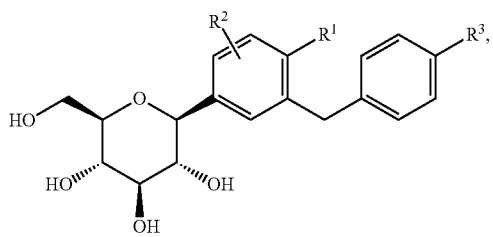

wherein $R^1$ denotes cyano, Cl or methyl,
$R^2$ denotes H, methyl, methoxy or hydroxy and
$R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano,
or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

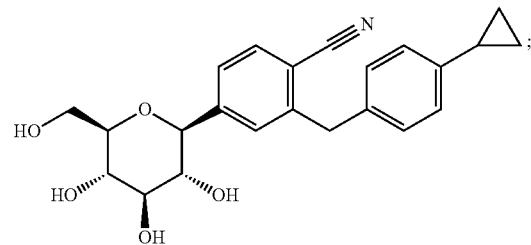 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

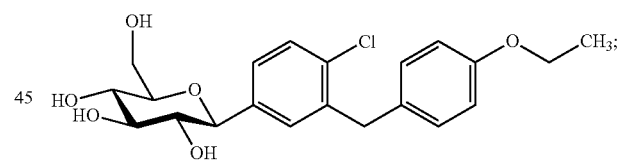

(4) Canagliflozin, represented by formula (4):

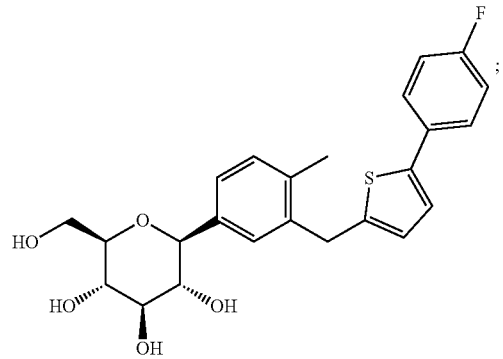 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):
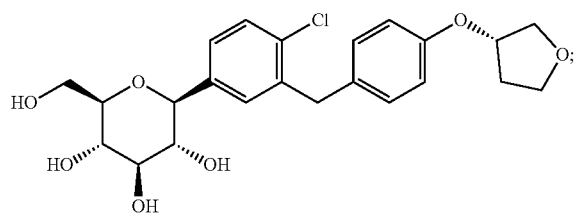 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
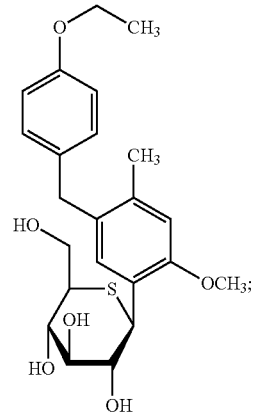
(7) Tofogliflozin, represented by formula (7):
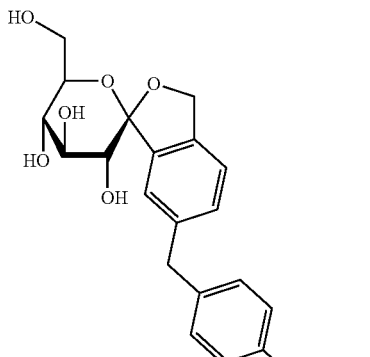
(8) Ipragliflozin, represented by formula (8):
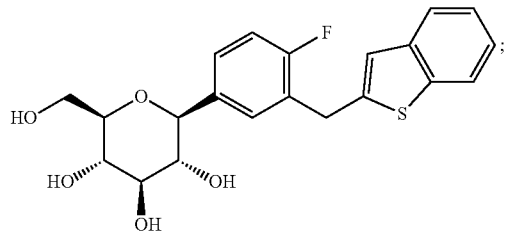 [SMILES: OC[C@H]1O[C@@H](c2ccc(F)c(Cc3cc4ccccc4s3)c2)[C@H](O)[C@@H](O)[C@@H]1O]
(9) Ertugliflozin, represented by formula (9):
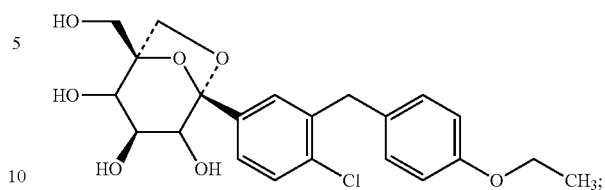
(10) Atigliflozin, represented by formula (10):
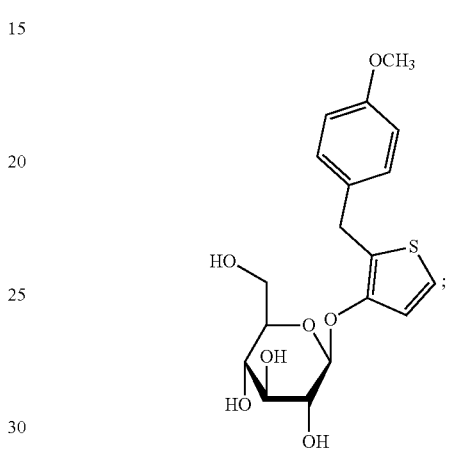
(11) Remogliflozin, represented by formula (11):
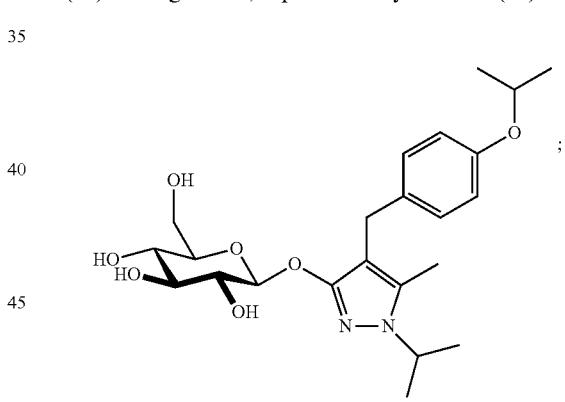
(11A) Remogliflozin etabonate, represented by formula (11A):
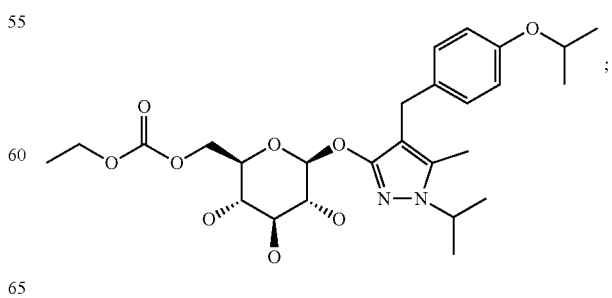

(12) a thiophene derivative of the formula (12)

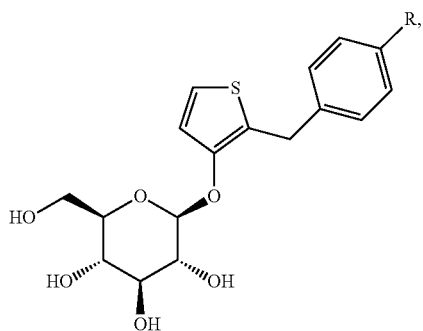

wherein R denotes methoxy or trifluoromethoxy;

(13) 1-(β-D-glucopyranosyl)-4-methyl-3-[5-(4-fluoro-phenyl)-2-thienylmethyl]benzene, represented by formula (13);

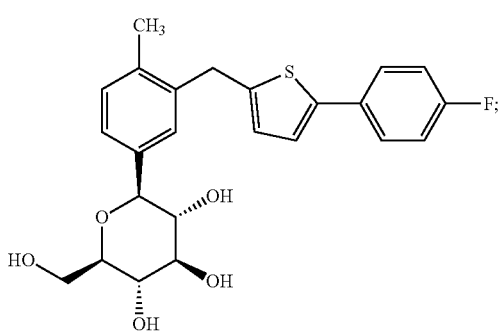 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

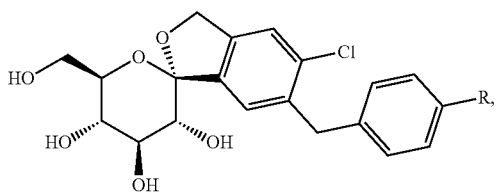

wherein R denotes methoxy, trifluoromethoxy, ethoxy, ethyl, isopropyl or tert-butyl;

(15) a pyrazole-O-glucoside derivative of the formula (15):

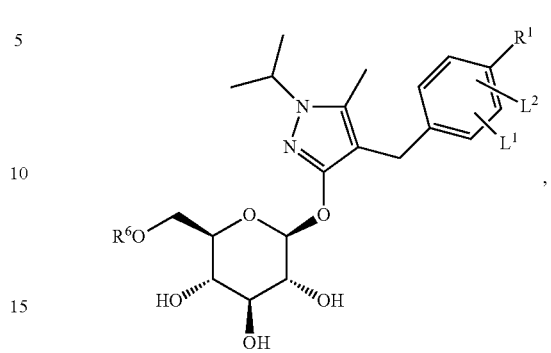

wherein
R¹ denotes $C_{1-3}$-alkoxy,
L¹, L² independently of each other denote H or F,
R⁶ denotes H, $(C_{1-3}$-alkyl)carbonyl, $(C_{1-6}$-alkyl)oxy-carbonyl, phenyloxycarbonyl, benzyloxycarbonyl or benzylcarbonyl;

(16) Sotagliflozin, represented by formula (16):

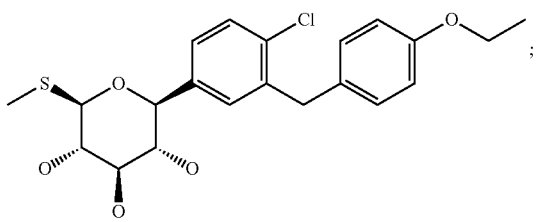 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

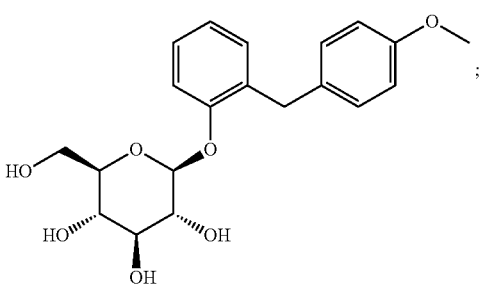

(18) a compound represented by formula (18):

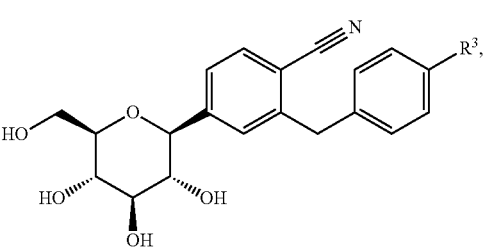

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxyethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano,
or a derivative thereof wherein one or more hydroxyl groups of the β-D-glucopyranosyl group are acylated with groups selected from (C$_{1-18}$-alkyl)carbonyl, (C$_{1-18}$-alkyl)oxycarbonyl, phenylcarbonyl and phenyl-(C$_{1-3}$-alkyl)-carbonyl;

(19) Bexagliflozin, represented by formula (19):

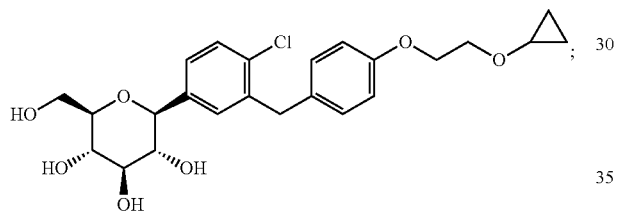

(20) Janagliflozin, represented by formula (20):

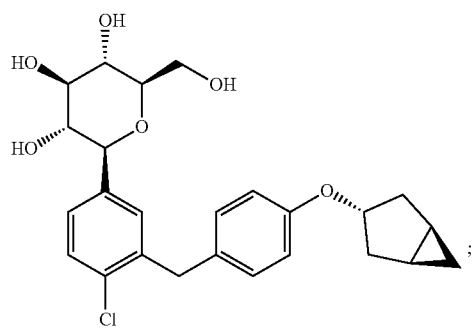 [SMILES: OC[C@H]1O[C@@H](c2ccc(Cl)c(Cc3ccc(O[C@H]4C[C@@H]5C[C@@H]5C4)cc3)c2)[C@H](O)[C@@H](O)[C@@H]1O]

(21) Rongliflozin; and
(22) Wanpagliflozin.

2. A method according to claim 1, wherein the at least one SGLT-2 inhibitor is administered in a therapeutically effective amount without exerting any harmful and/or abortifacient effects on a pregnant non-human mammal, and/or wherein the at least one SGLT-2 inhibitor is administered in a therapeutically effective amount without exerting any negative effects on the subsequent reproduction cycle/fertility and milk yield and/or milk quality in the next lactation.

3. The method according to claim 2, wherein the at least one SGLT-2 inhibitor is administered in a therapeutically effective amount that additionally or alternatively effects a reduction of the incidence of new intra-mammary infections (IMI) or mastitis in the first month after start of the next lactation.

4. The method according to claim 1, wherein the non-human mammal is selected from the group consisting of: bovine, canine, caprine, equine, feline, lagomorphs, ovine, porcine, and rodent.

5. The method according to claim 1, wherein the at least one SGLT-2 inhibitor is administered orally, parenterally, rectally, intravaginally, intravenously, subcutaneously or intramuscularly.

6. The method according to claim 1, wherein the at least one SGLT-2 inhibitor is administered at a dose of 0.01 mg/kg bodyweight to 10 mg/kg bodyweight.

7. The method according to claim 1, wherein the at least one SGLT-2 inhibitor is administered once, twice, three-times, four-times, five-times, six-times or daily for a week.

8. The method according to claim 1, wherein the at least one SGLT-2 inhibitor is administered once only at start of drying-off or twice as two treatments 24 hours or 48 hours apart after last milking.

9. The method according to claim 1, wherein the non-human mammal is a cow, a pregnant cow, and/or a lactating cow.

10. The method according to claim 1, wherein the at least one SGLT-2 inhibitor comprises Velagliflozin, represented by formula:

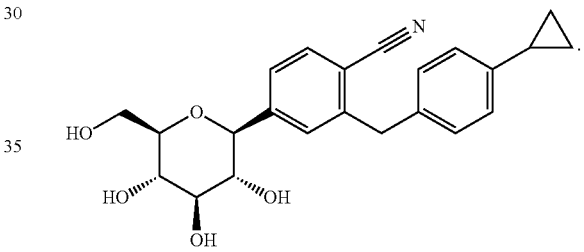

11. A method of reducing milk production in a pregnant and/or lactating non-human mammal, comprising administering to the non-human mammal at least one SGLT-2 inhibitor, wherein the at least one SGLT-2 inhibitor is selected from the group consisting of:
(1) a glucopyranosyl-substituted benzene derivative of the formula (1)

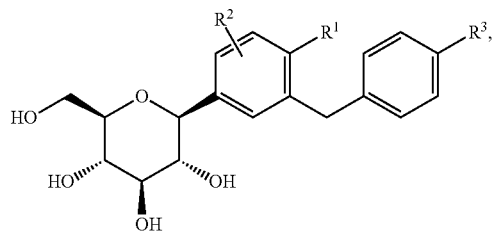

wherein R¹ denotes cyano, Cl or methyl,
R² denotes H, methyl, methoxy or hydroxy and
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

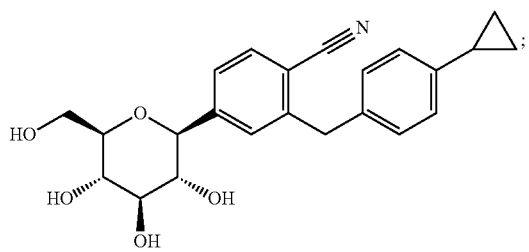 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

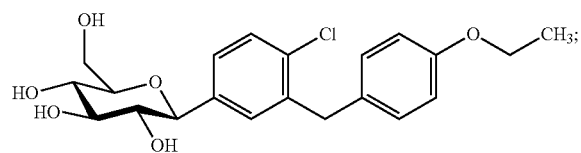

(4) Canagliflozin, represented by formula (4):

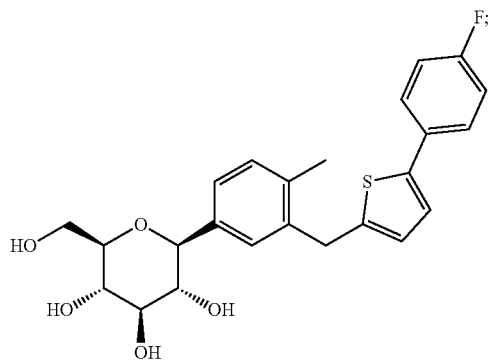 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

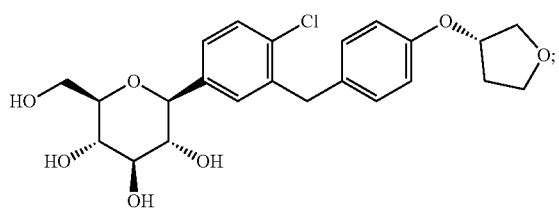 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

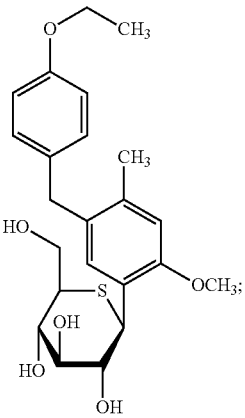

(7) Tofogliflozin, represented by formula (7):

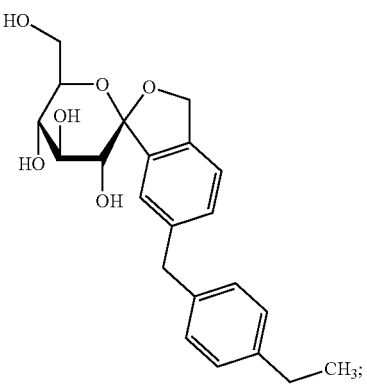

(8) Ipragliflozin, represented by formula (8):

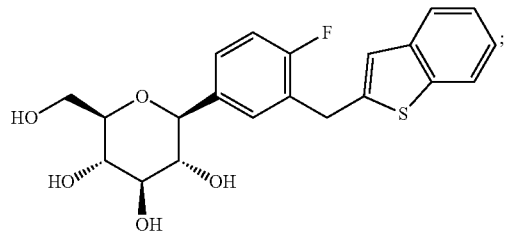 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

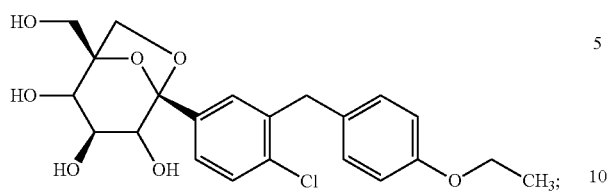

(10) Atigliflozin, represented by formula (10):

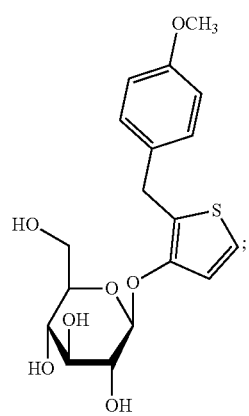

(11) Remogliflozin, represented by formula (11):

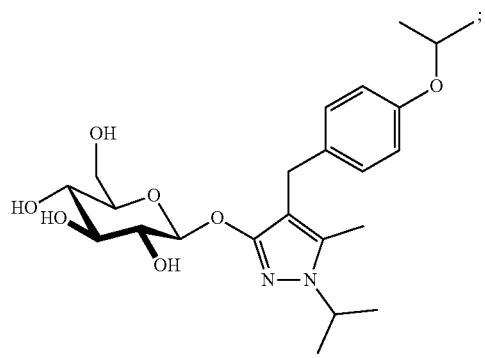

(11A) Remogliflozin etabonate, represented by formula (11A):

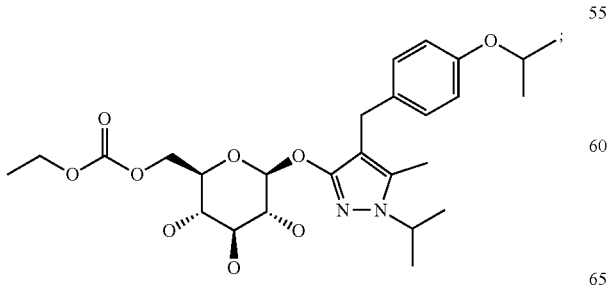

(12) a thiophene derivative of the formula (12)

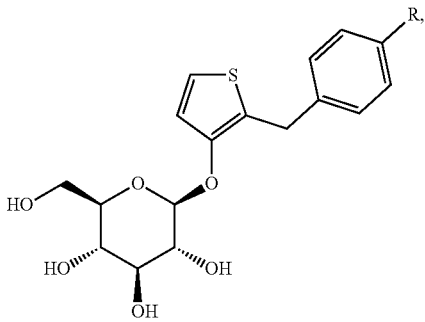

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

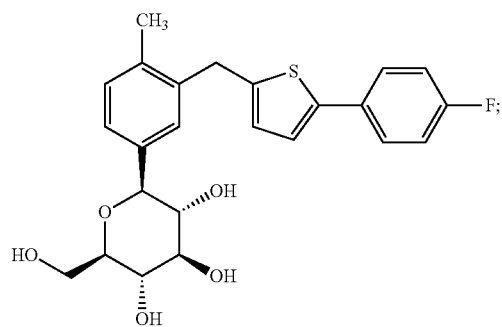 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

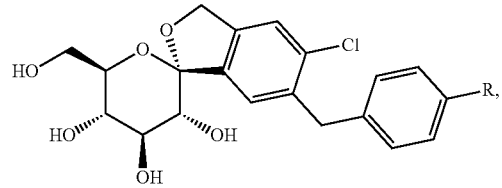

wherein R denotes methoxy, trifluoromethoxy, ethoxy, ethyl, isopropyl or tert-butyl;

(15) a pyrazole-O-glucoside derivative of the formula (15):

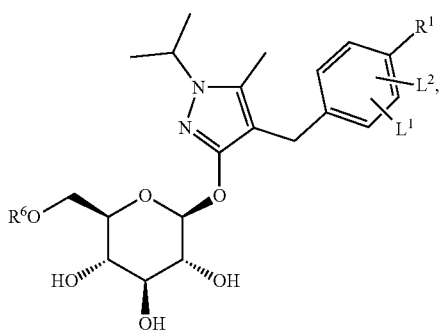

wherein
R¹ denotes $C_{1-3}$-alkoxy,
L¹, L² independently of each other denote H or F,
R⁶ denotes H, $(C_{1-3}$-alkyl)carbonyl, $(C_{1-6}$-alkyl)oxycarbonyl, phenyloxycarbonyl, benzyloxycarbonyl or benzylcarbonyl;

(16) Sotagliflozin, represented by formula (16):

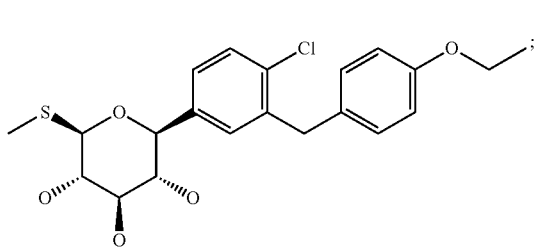 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

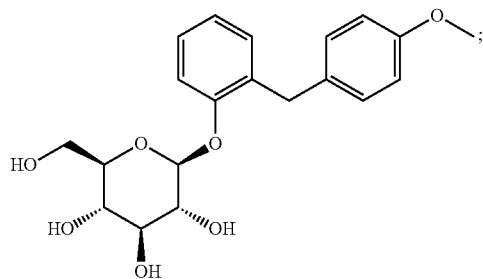 [SMILES: COc1ccc(Cc2ccccc2O[C@@H]2O[C@H](CO)[C@@H](O)[C@H](O)[C@H]2O)cc1]

(18) a compound represented by formula (18):

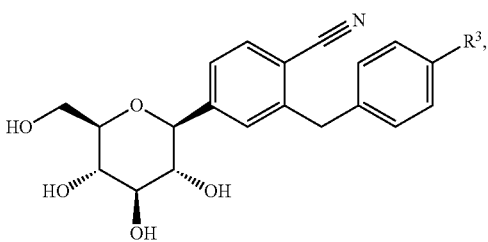

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methylsulfonyl, ethylsulfinyl, ethylsulfonyl, trimethylsilyl, (R)-tetrahydrofuran-3-yloxy or (S)-tetrahydrofuran-3-yloxy or cyano,
or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(19) Bexagliflozin, represented by formula (19):

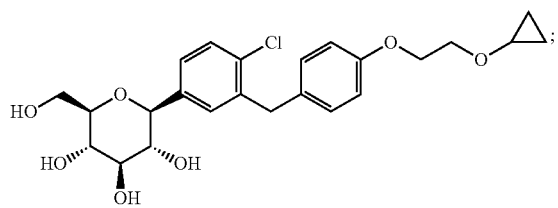 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

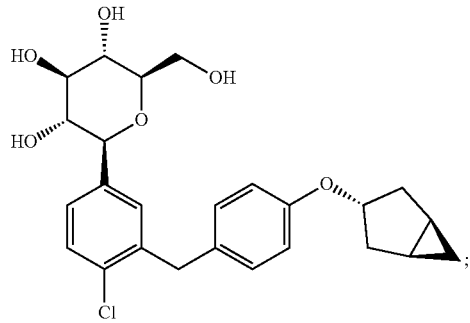 [SMILES: OC[C@H]1O[C@@H](c2ccc(Cl)c(Cc3ccc(O[C@H]4C[C@@H]5C[C@@H]5C4)cc3)c2)[C@H](O)[C@@H](O)[C@@H]1O]

(21) Rongliflozin; and
(22) Wanpagliflozin.

12. A method of decreasing milk accumulation and/or engorgement in the udder and/or mammary gland of a non-human mammal, comprising administering to the non-human mammal at least one SGLT-2 inhibitor, wherein the at least one SGLT-2 inhibitor is selected from the group consisting of:
(1) a glucopyranosyl-substituted benzene derivative of the formula (1)

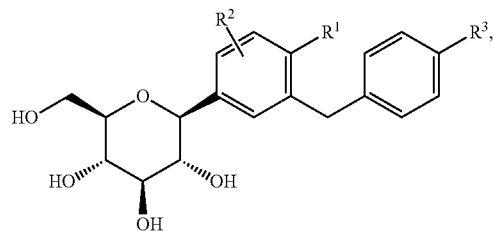

wherein R¹ denotes cyano, Cl or methyl,
R² denotes H, methyl, methoxy or hydroxy and
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro- 1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

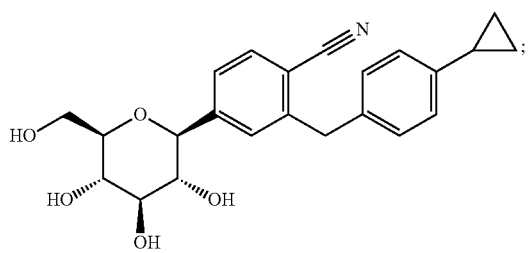 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

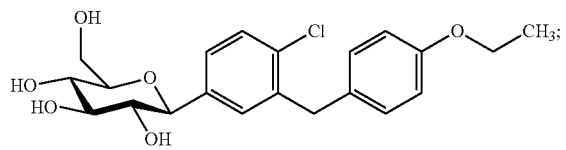

(4) Canagliflozin, represented by formula (4):

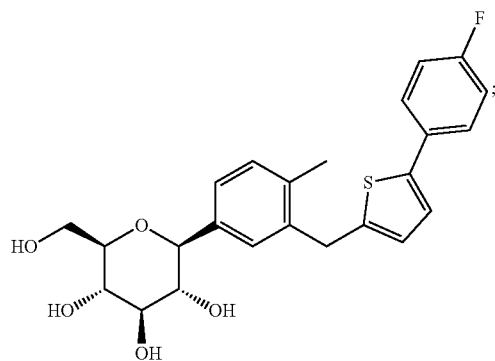 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

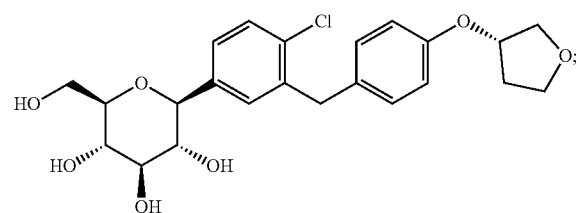 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

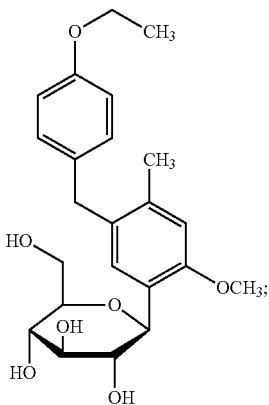

(7) Tofogliflozin, represented by formula (7):

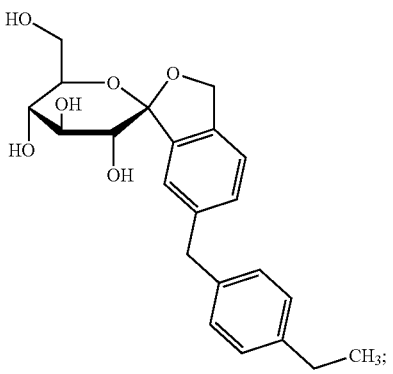

(8) Ipragliflozin, represented by formula (8):

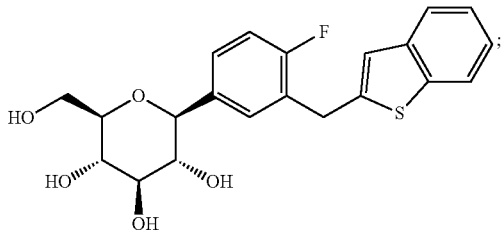 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

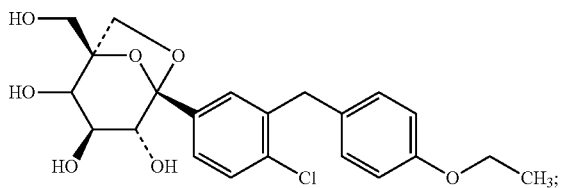

(10) Atigliflozin, represented by formula (10):

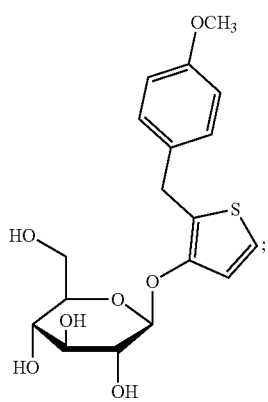

(11) Remogliflozin, represented by formula (11):

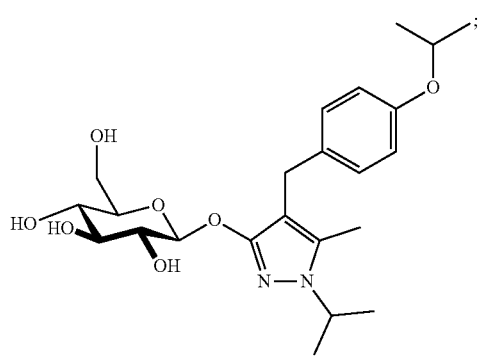

(11A) Remogliflozin etabonate, represented by formula (11A):

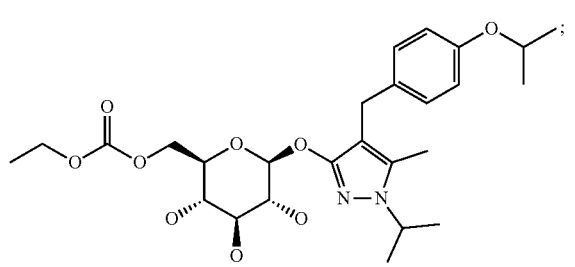 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

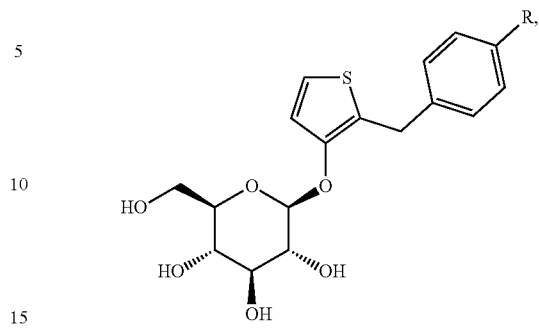

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

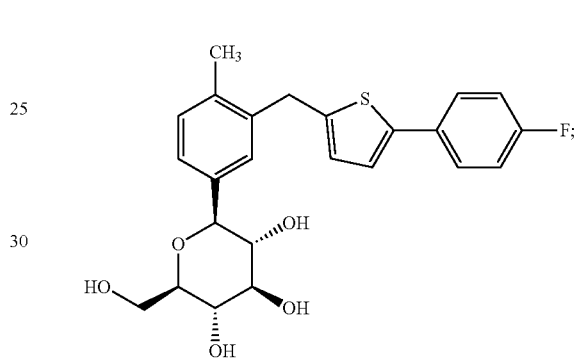

(14) a spiroketal derivative of the formula (14):

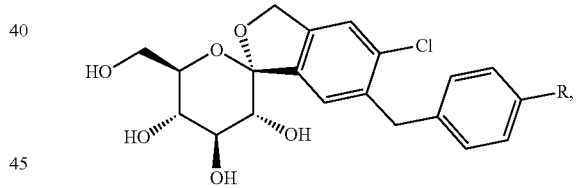

wherein R denotes methoxy, trifluoromethoxy, ethoxy, ethyl, isopropyl or tert-butyl;

(15) a pyrazole-O-glucoside derivative of the formula (15):

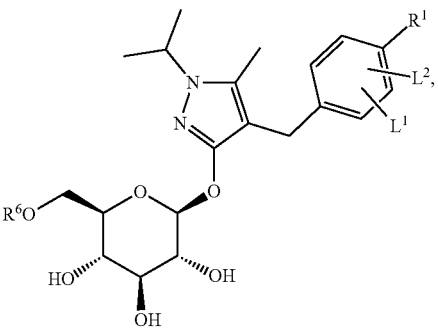

wherein
R¹ denotes $C_{1-3}$-alkoxy,
L¹, L² independently of each other denote H or F,
R⁶ denotes H, ($C_{1-3}$-alkyl)carbonyl, ($C_{1-6}$-alkyl)oxycarbonyl, phenyloxycarbonyl, benzyloxycarbonyl or benzylcarbonyl:

(16) Sotagliflozin, represented by formula (16):

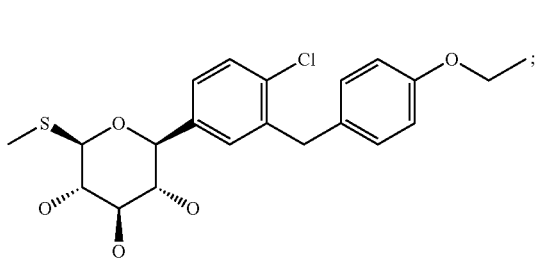 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

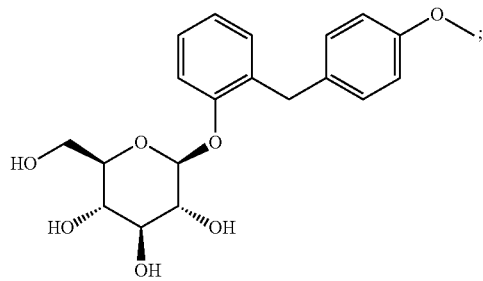 [SMILES: COc1ccc(Cc2ccccc2O[C@@H]2O[C@H](CO)[C@@H](O)[C@H](O)[C@H]2O)cc1]

(18) a compound represented by formula (18):

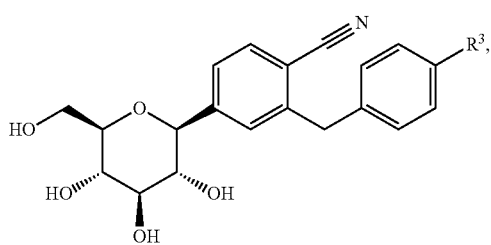

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methylsulfonyl, ethylsulfinyl, ethylsulfonyl, trimethylsilyl, (R)-tetrahydrofuran-3-yloxy or (S)-tetrahydrofuran-3-yloxy or cyano,
or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

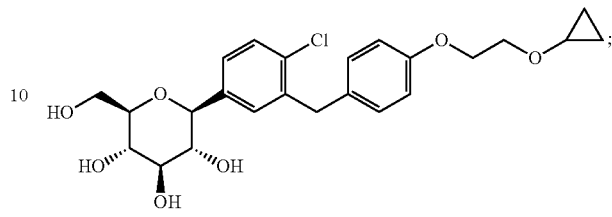

(20) Janagliflozin, represented by formula (20):

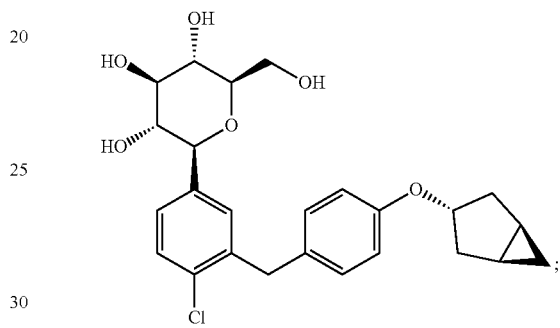

(21) Rongliflozin; and
(22) Wanpagliflozin.

13. The method according to claim 12, wherein the at least one SGLT-2 inhibitor comprises Velagliflozin, represented by formula:

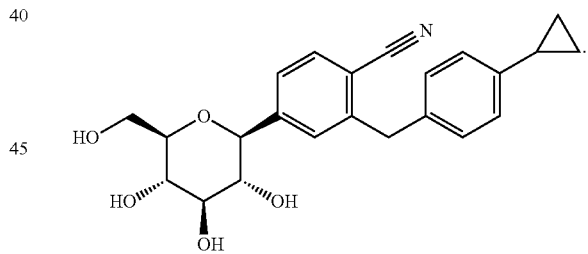

14. A method of decreasing the discomfort associated with udder engorgement of a non-human mammal, comprising administering to the non-human mammal at least one SGLT-2 inhibitor.

15. A method of decreasing milk leakage after drying-off of a non-human mammal, comprising administering to the non-human mammal at least one SGLT-2 inhibitor.

16. A method of decreasing an incidence of intra-mammary infections (IMI) in a non-human mammal, comprising administering to the non-human mammal at least one SGLT-2 inhibitor.

17. The method according to any one of claims 14, wherein the at least one SGLT-2 inhibitor is selected from the group consisting of:
(1) a glucopyranosyl-substituted benzene derivative of the formula (1)

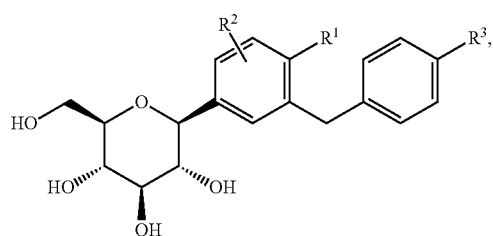

wherein R¹ denotes cyano, Cl or methyl;

R² denotes H, methyl, methoxy or hydroxy and

R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, or a derivative thereof wherein one or more hydroxyl groups of the β-D-glucopyranosyl group are acylated with groups selected from (C₁₋₁₈-alkyl)carbonyl, (C₁₋₁₈-alkyl)oxycarbonyl, phenylcarbonyl and phenyl-(C₁₋₃-alkyl)-carbonyl;

(2) Velagliflozin, represented by formula (2):

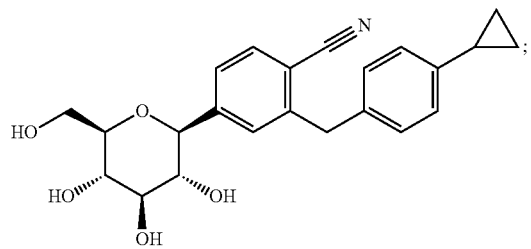 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

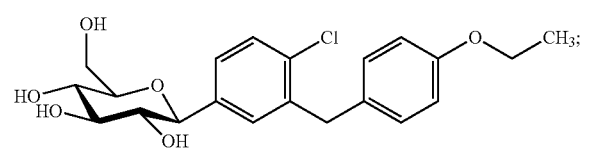

(4) Canagliflozin, represented by formula (4):

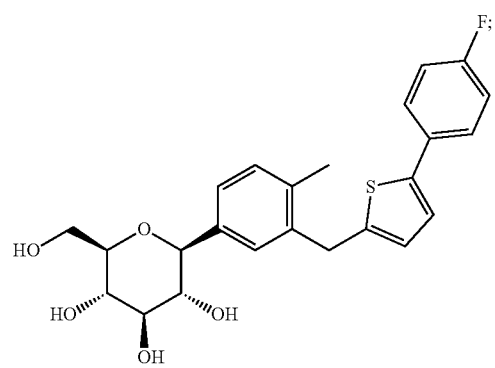 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

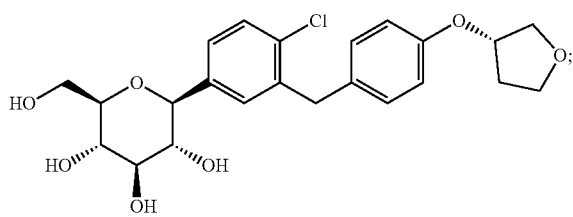 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

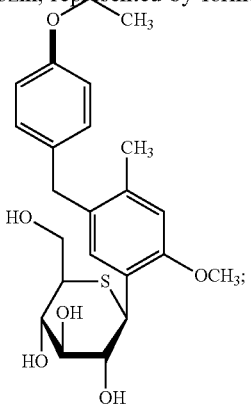

(7) Tofogliflozin represented by formula (7):

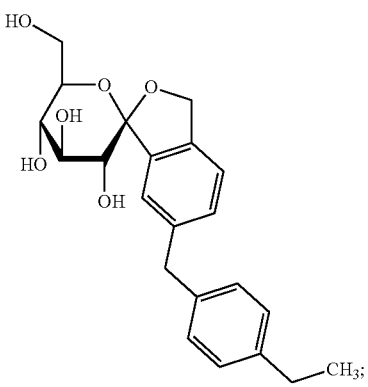

(8) Ipragliflozin, represented by formula (8):

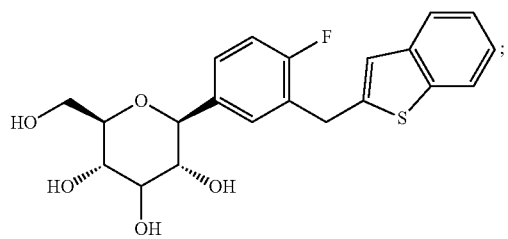 [SMILES: OC[C@H]1O[C@@H](c2ccc(F)c(Cc3cc4ccccc4s3)c2)[C@H](O)C(O)[C@@H]1O]

(9) Ertugliflozin, represented by formula (9):

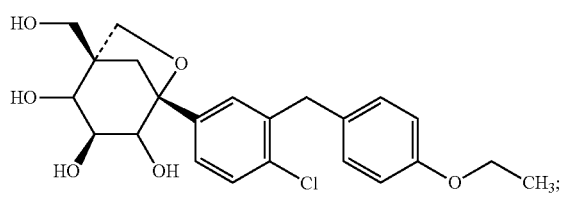 [SMILES: CCOc1ccc(Cc2cc([C@@]34C[C@@](CO)(CO3)C(O)[C@H](O)C4O)ccc2Cl)cc1]

(10) Atigliflozin, represented by formula (10):

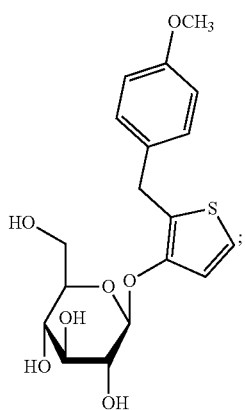

(11) Remogliflozin represented by formula (11):

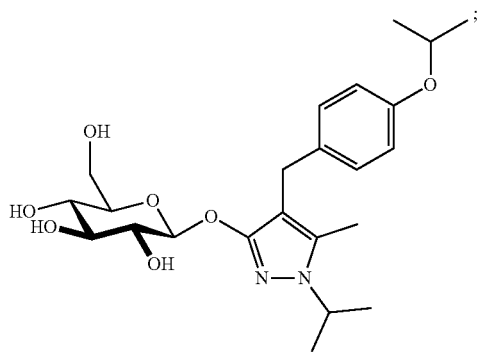

(11A) Remogliflozin etabonate, represented by formula (11A):

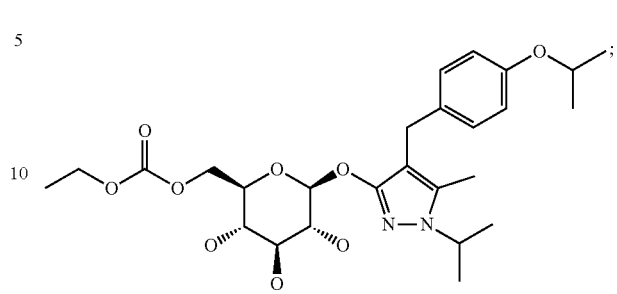

(12) a thiophene derivative of the formula (12)

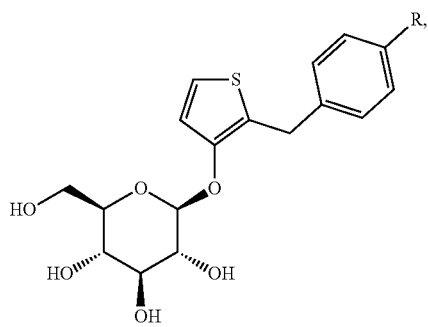

wherein R denotes methoxy or trifluoromethoxy;

(13)  1-(β-D-glucopyranosyl)-4-methyl-3-[5-(4-fluorophenyl)-2-thienylmethyl]benzene, represented by formula (13);

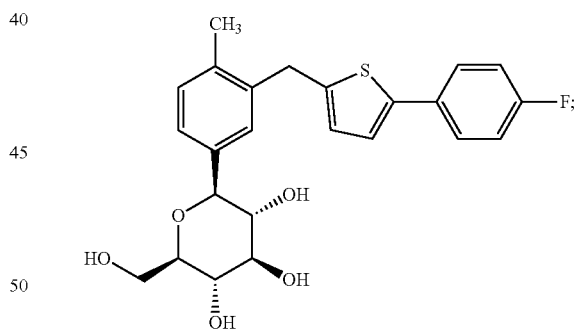

(14) a spiroketal derivative of the formula (14):

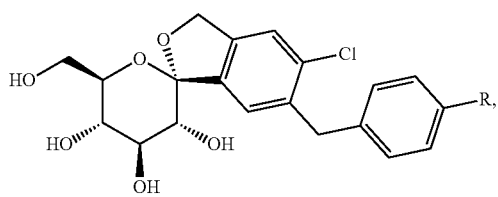

wherein R denotes methoxy, trifluoromethoxy, ethoxy, ethyl, isopropyl or tert-butyl;

(15) a pyrazole-O-glucoside derivative of the formula (15):

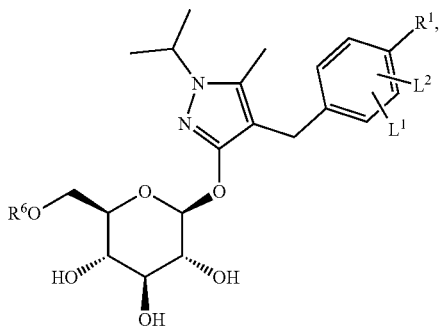

wherein
R¹ denotes $C_{1-3}$-alkoxy,
L¹, L² independently of each other denote H or F,
R⁶ denotes H, ($C_{1-3}$-alkyl)carbonyl, ($C_{1-6}$-alkyl)oxycarbonyl, phenyloxycarbonyl, benzyloxycarbonyl or benzylcarbonyl;

(16) Sotagliflozin, represented by formula (16):

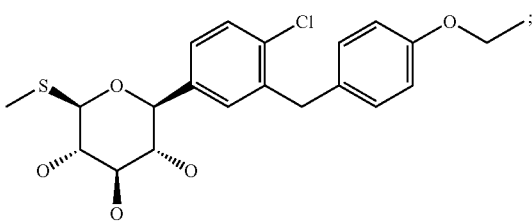 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

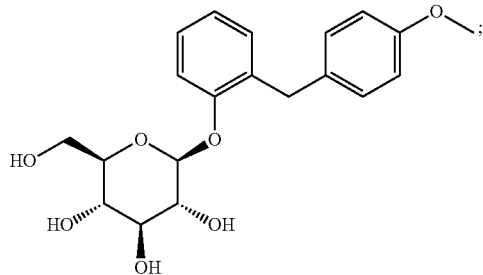 [SMILES: COc1ccc(Cc2ccccc2O[C@@H]2O[C@H](CO)[C@@H](O)[C@H](O)[C@H]2O)cc1]

(18) a compound represented by formula (18):

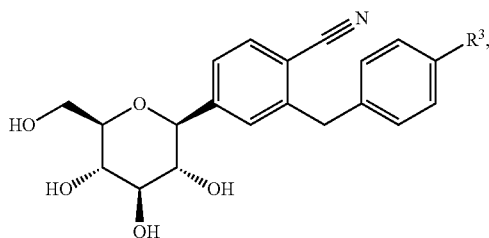

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

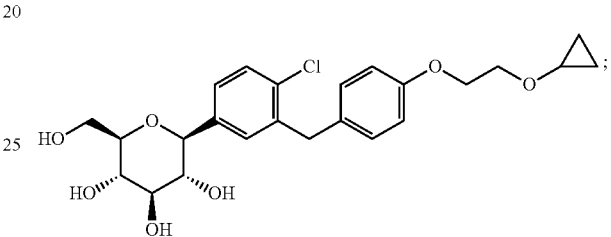

(20) Janagliflozin, represented by formula (20):

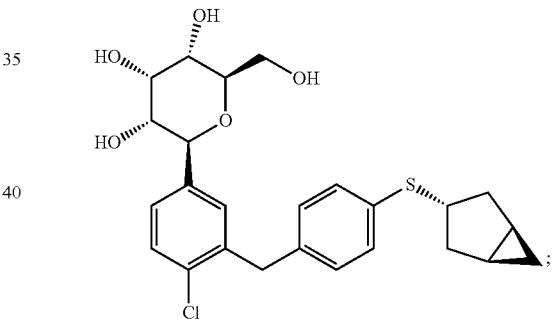

(21) Rongliflozin; and
(22) Wanpagliflozin.

18. The method according to claim 14, wherein the method of decreasing the discomfort associated with udder engorgement of a non-human mammal is increasing the daily lying time and/or reduction of stress.

19. The method according to claim 16, wherein the intra-mammary infections (IMI) are mastitis and/or metritis.

20. A method of improving and/or facilitating the drying-off of a non-human mammal, comprising administering to the non-human mammal velagliflozin as a single SGLT-2 inhibitor, wherein velagliflozin is administered subcutaneously or intramuscularly, once only at start of drying-off or twice (24 h or 48 h apart) at a dose of 0.01 mg/kg bodyweight to 10 mg/kg bodyweight.

21. The method according to claim 20, wherein the at least one SGLT-2 inhibitor is administered before, after or concomitantly with administering at least one feed supplement to the non-human mammal and/or before, after or concomitantly with a reduction in feed offered to the non-human mammal.

22. The method according to claim 21, wherein the feed supplement comprises one or more acidifying agents selected from the group consisting of: ammonium chloride, calcium chloride and calcium sulfate.

23. The method according to claim 22, wherein the feed supplement comprises 5% (w/w) to 15% (w/w) ammonium chloride, 40% (w/w) to 60% (w/w) calcium chloride and 15% (w/w) to 25% (w/w) calcium sulfate.

24. The method according to claim 22, wherein the feed supplement comprises 10.4% (w/w) ammonium chloride, 51.9% (w/w) calcium chloride and 20.1% (w/w) calcium sulfate.

25. The method according to claim 20, wherein the non-human mammal is a cow, a pregnant cow, and/or a lactating cow.

* * * * *